(12) United States Patent
Zheng et al.

(10) Patent No.: US 8,933,243 B2
(45) Date of Patent: *Jan. 13, 2015

(54) POLYPHENYLENE HOST COMPOUNDS

(75) Inventors: Shijun Zheng, San Diego, CA (US); Liping Ma, San Diego, CA (US); Amane Mochizuki, Carlsbad, CA (US); Qianxi Lai, Vista, CA (US); Sazzadur Rahman Khan, San Diego, CA (US); Sheng Li, Vista, CA (US); Brett T. Harding, Carlsbad, CA (US); Hyunsik Chae, San Diego, CA (US); Rebecca Romero, Escondido, CA (US); David T. Sisk, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 165 days.

This patent is subject to a terminal disclaimer.

(21) Appl. No.: 13/166,246

(22) Filed: Jun. 22, 2011

(65) Prior Publication Data

US 2011/0251401 A1    Oct. 13, 2011

(51) Int. Cl.
| | | |
|---|---|---|
| C07D 235/18 | (2006.01) | |
| C07D 403/10 | (2006.01) | |
| C07D 409/04 | (2006.01) | |
| H01L 51/00 | (2006.01) | |
| H01L 51/50 | (2006.01) | |

(52) U.S. Cl.
CPC .......... *C07D 235/18* (2013.01); *C07D 403/10* (2013.01); *C07D 409/04* (2013.01); *H01L 51/006* (2013.01); *H01L 51/0072* (2013.01); *H01L 51/0037* (2013.01); *H01L 51/0085* (2013.01); *H01L 51/5016* (2013.01)
USPC ........................................................ 548/310.7

(58) Field of Classification Search
None
See application file for complete search history.

(56) References Cited

U.S. PATENT DOCUMENTS

| | | | |
|---|---|---|---|
| 6,232,322 | B1 | 5/2001 | Malamas et al. |
| 6,620,529 | B1 | 9/2003 | Ise et al. |
| 6,835,469 | B2 | 12/2004 | Kwong et al. |
| 7,851,074 | B2 | 12/2010 | Kido et al. |
| 2006/0012312 | A1 | 1/2006 | Lyle, Jr. et al. |
| 2008/0014464 | A1 | 1/2008 | Kawamura et al. |
| 2009/0134783 | A1 | 5/2009 | Lin et al. |
| 2010/0060154 | A1 | 3/2010 | Nomura et al. |
| 2011/0140093 | A1 | 6/2011 | Zheng et al. |
| 2011/0251401 | A1 | 10/2011 | Zheng et al. |

FOREIGN PATENT DOCUMENTS

| | | |
|---|---|---|
| EP | 0 499 222 | 2/1992 |
| JP | 59075257 A | 4/1984 |
| JP | 64009959 | 1/1989 |
| JP | 7-076542 A | 3/1995 |
| JP | 7207169 | 8/1995 |
| JP | 2000095766 A | 4/2000 |
| JP | 2001023777 A | 1/2001 |
| JP | 2001247858 A | 9/2001 |
| JP | 2002275179 A | 9/2002 |
| KR | 2009073852 A | 7/2009 |
| KR | 2009114008 A | 11/2009 |
| KR | 959189 B1 | 5/2010 |
| KR | 2010075079 A | 7/2010 |
| WO | WO 99/58518 A2 | 11/1999 |
| WO | WO 2004/010996 A1 | 2/2004 |
| WO | WO 2004/020388 | 3/2004 |
| WO | WO 2010/044607 | 4/2010 |

OTHER PUBLICATIONS

Chen, et al., "Versatile, Benzimidazole/Amine-Based Ambipolar Compounds for Electroluminescent Applications: Single-Layer, Blue, Fluorescent OLEDs, Hosts for Single-Layer, Phosphorescent OLEDs ", Advanced Functional Materials (2009), 19(16), 2661-2670.

Debeaux, Marc, et al., "Charge-Transporting Polymers based on Phenylbenzoimidazole Moieties", Advanced Functional Materials (2010), 20(3), 399-408.

Gong, Shalong, et al., "Versatile Benzimidazole/Triphenylamine Hybrids: Efficient Nondoped Deep-Blue Electroluminescence and Good Host Materials for Phosphorescent Emitters", Chemistry-An Asian Journal (2010), 5(9), 2093-2099.

Bipolar anthracene derivatives containing hole- and electron-transporting moieties for highly efficient blue electroluminescence devices by Huang, Jinhai; Su, Jian-Hua; Li, Xin; Lam, Mei-Ki; Fung, Ka-Man; Fan, Hai-Hua; Cheah, Kok-Wai; Chen, Chin H.; Tian, He. Journal of Materials Chemistry (2011), 21(9), 2957-2964. Language: English, Database: CAPLUS.

Ge, Ziyi et al., "Solution-Processible Bipolar Triphenylamine-Benzimidazole Derivatives for Highly Efficient Single-Layer Organic Light-Emitting Diodes", Chemistry of Materials, 20 (7), 2532-2537, XP002608601 Mar. 11, 2008.

Ge, Ziyi et al., "Spin-Coated Highly Efficient Phosphorescent Organic Light-Emitting Diodes Based on Bipolar Triphenylamine-Benzimidazole Derivatives", Advanced Functional Materials, vol. 18, No. 4, Feb. 22, 2008, pp. 584-590, XP001510816, Wiley, ISSN:1616-301X.

Gustafsson, Flexible Light-emitting diodes made from soluble conducting polymer, Nature, vol. 357, pp. 477-479 (Jun. 11, 1992).

Kauffman, et al., Synthesis and photophysical properties of fluorescent 2-aryl-1,3-dialkylbenzimidazolium ions and a 1-alkyl-2-arylbenzimidazole with excited state intramolecular proton-transfer. Journal of Heterocyclic Chemistry (1994), 31(4), 957-65.

Kim, et al., Synthesis and properties of highly fluorescent liquid crystals containing bexzoxazole moeity, Molecular Crystals and Liquid Crystals Science and Technology, Section A, No. 337, pp. 405-408, 1999.

(Continued)

*Primary Examiner* — Alicia L Otton
(74) *Attorney, Agent, or Firm* — K&L Gates LLP; Louis C. Cullman; Brent A. Johnson

(57) ABSTRACT

Polyphenylene compounds such as compounds represented by Formula I may be used in electronic devices such as organic light-emitting devices. For example, the compounds may be used as host materials in a light-emitting layer.

3 Claims, 2 Drawing Sheets

(56) References Cited

OTHER PUBLICATIONS

Li et al., "Synthesis and Functional Properties of Strongly Luminescent Diphenylamino End-Capped Oligophenylenes" Journal of Organic Chemistry, American Chemical Society, vol. 69, No. 3, pp. 921-927, Feb. 6, 2004.

Malamas, et al., Novel Benzofuran and Benzothiophene Biphenyls as Inhibitors of Protein Tyrosine Phosphatase 1B with Antihyperglycemic Properties. Journal of Medicinal Chemistry (2000), 43(7), 1293-1310.

Ueda, et al., Synthesis of poly(benzothiazole)s by direct polycondensation of dicarboxylic acids with 2,5-diamino-1,4-benzenedithiol dihydrochloride using phosphorus pentoxide/methaneusulfonic acid as condensing agent and solvent, Polymer Journal vol. 18, No. 2, 1986 pp. 117-122.

Vinodkumar, et al., Synthesis of highly functionalized 2-(substituted biphenyl)benzimidazoles via Suzuki-Miyaura cross-coupling reaction. Journal of Heterocyclic Chemistry (2007), 44(6), 1521-1523.

Li, Zong Hou, et al., Synthesis and blue light-emitting properties of 4,4'-bis(diphenylamino)-quinquie(p-phenyl)s. Chinese Chemical Letters, 18(7): 823-826 (2007).

International Preliminary Report on Patentability and Written Opinion for International Application No. PCT/US2012/043595 mailed on Jan. 9, 2014.

POLYPHENYLENE HOST COMPOUNDS

BACKGROUND

1. Field of the Invention

The embodiments relate to host compounds for light-emitting layers in devices.

2. Description of the Related Art

Organic light-emitting devices (OLEDs) are becoming increasingly important in lighting and display applications. OLEDs may include an emissive or light-emitting layer that includes a host material and a light-emitting component dispersed within the host material. Host materials in OLEDs may have problems with low stability, a high charge-injection barrier, and imbalanced charge injection and mobility. These potential deficiencies with host materials may contribute to low efficiency and short lifetime of the devices comprising the host materials.

SUMMARY

Some embodiments include a compound represented by Formula 1:

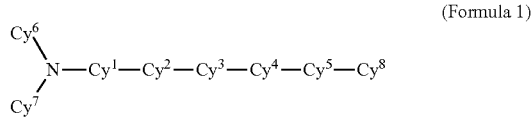

(Formula 1)

wherein $Cy^1$, $Cy^2$, $Cy^3$, $Cy^4$, and $Cy^5$ are independently optionally substituted p-phenylene; $Cy^6$ is optionally substituted phenyl; $Cy^7$ is optionally substituted phenyl or optionally substituted naphthalenyl, wherein $Cy^6$ and $Cy^7$ optionally link together to form a third ring comprising the N to which they are attached; and $Cy^8$ is optionally substituted 1-phenyl-1H-benzo[d]imidazol-2-yl.

With respect to Formula 1, in some embodiments $Cy^1$, $Cy^2$, $Cy^3$, $Cy^4$, and $Cy^5$ are independently p-phenylene optionally substituted with 1 or 2 substituents independently selected from $C_{1-6}$ alkyl and F; $Cy^6$ is phenyl optionally substituted with 1, 2, or 3 substituents independently selected from $C_{1-6}$ alkyl and F; $Cy^7$ is naphthalen-1-yl optionally substituted with 1, 2, or 3 substituents independently selected from $C_{1-6}$ alkyl and F; and $Cy^8$ is 1-phenyl-1H-benzo[d]imidazol-2-yl optionally substituted with 1, 2, 3, 4, or 5 substituents independently selected from $C_{1-6}$ alkyl and F.

Some embodiments include optionally substituted penta(para-phenylenyl) compounds, including optionally substituted 1-(1-phenyl-1H-benzo[d]imidazol-2-yl)-[4$^e$-phenyl (naphthalen-1-yl)amino]penta(para-phenylenyl); optionally substituted 1-(1-phenyl-1H-benzo[d]imidazol-2-yl)-[4$^e$-(carbazol-9-yl)amino]penta(para-phenylenyl); optionally substituted 1-(1-phenyl-1H-benzo[d]imidazol-2-yl)-[4$^e$-diphenylamino]penta(para-phenylenyl); optionally substituted 1-(1-phenyl-1H-benzo[d]imidazol-2-yl)-[4$^e$-phenyl (naphthalen-2-yl)amino]penta(para-phenylenyl); optionally substituted 1-(1-phenyl-1H-benzo[d]imidazol-2-yl)-[4$^e$-di (4-methylphenyl)amino]penta(para-phenylenyl); etc.

Some embodiments include a light-emitting device comprising a compound described herein.

These and other embodiments are described in more detail herein.

DETAILED DESCRIPTION

Figure 1:
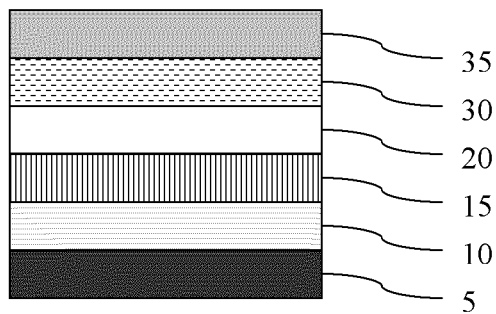
FIG. 1 is a schematic drawing of an embodiment of an OLED comprising a compound disclosed herein.

Unless otherwise indicated, when a compound or chemical structural feature such as aryl is referred to as being "optionally substituted," it is meant that the feature may have no substituent (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc. In some embodiments, two substituents may combine to form a ring. In some embodiments, a substituent may be a linking group that is attached to two or more structural features, e.g., a substituent can be a linking substituent so that $Cy^1$, $Cy^2$, and the linking substituent (e.g., alkyl, —O—, —NH—, etc.) form a fused tricyclic ring system as described in greater detail herein.

Structures associated with some of the chemical names referred to herein are depicted below. These structures may be unsubstituted, as shown below, or a substituent may independently be in any position normally occupied by a hydrogen atom when the structure is unsubstituted.

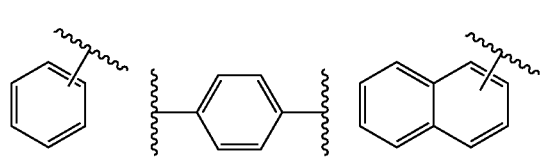
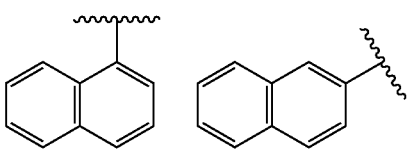
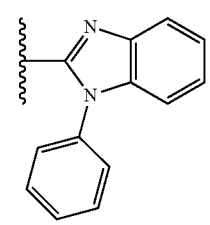
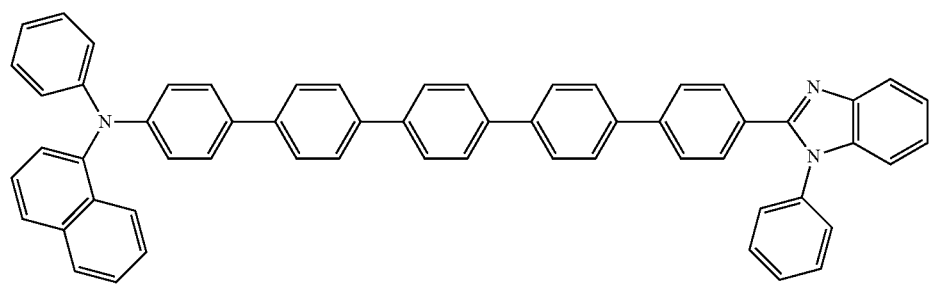
1-(1-phenyl-1H-benzo[d]imidazol-2-yl)-[4$^e$-phenyl(naphthalen-1-yl)amino]penta(para-phenylenyl)
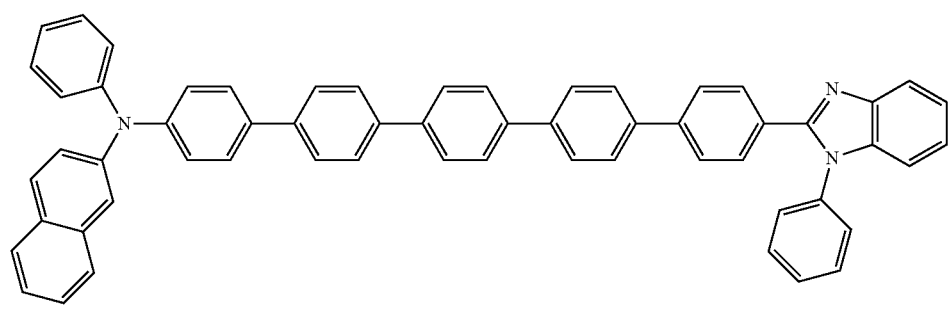
1-(1-phenyl-1H-benzo[d]imidazol-2-yl)-[4$^e$-phenyl(naphthalen-2-yl)amino]penta(para-phenylenyl)
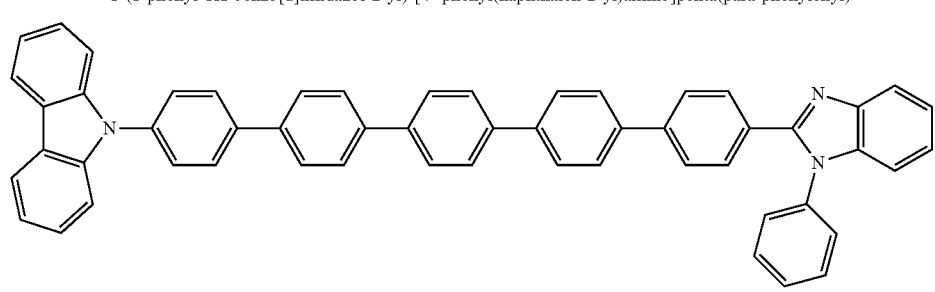
1-(1-phenyl-1H-benzo[d]imidazol-2-yl)-[4$^e$-(carbazol-9-yl)amino]penta(para-phenylenyl)
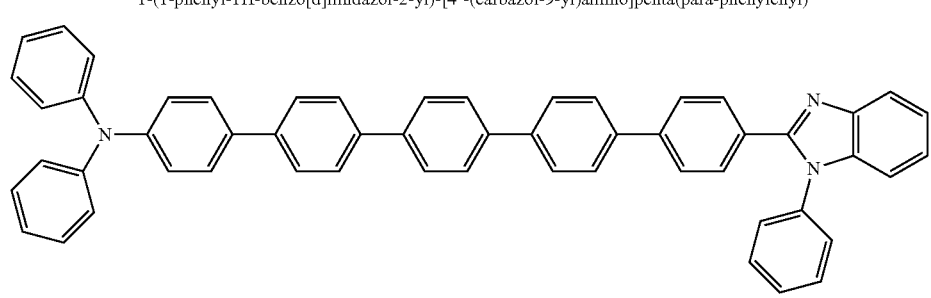
1-(1-phenyl-1H-benzo[d]imidazol-2-yl)-[4$^e$-diphenylamino]penta(para-phenylenyl)

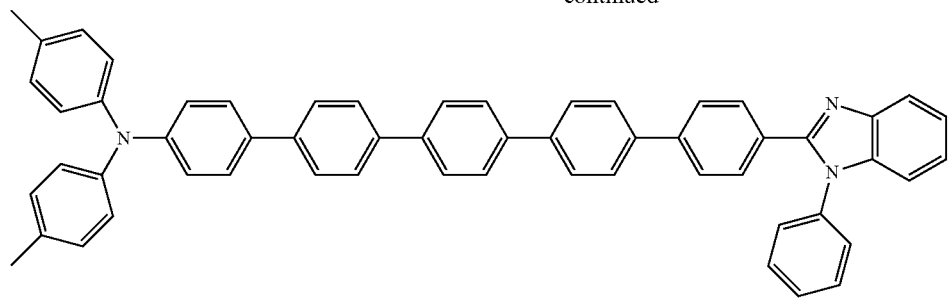

1-(1-phenyl-1H-benzo[d]imidazol-2-yl)-[4$^e$-di(4-methylphenyl)amino]penta(para-phenylenyl)

As used herein the term "alkyl" has the ordinary meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like. In some embodiments, alkyl may be a linking group that is attached to two or more structural features, e.g., alkyl may be a linking substituent so that $Cy^1$, $Cy^2$, and the linking substituent form a fused tricyclic ring system as described in greater detail below.

As used herein, the term "alkoxy" includes —O-alkyl, such as —$OCH_3$, —$OC_2H_5$, —$OC_3H_7$ (e.g. propoxy isomers such as isopropoxy, n-propoxy, etc.), —$OC_4H_9$ (e.g. butyoxy isomers), —$OC_5H_{11}$ (e.g. pentoxy isomers), —$OC_6H_{13}$ (e.g. hexoxy isomers), —$OC_7H_{15}$ (e.g. heptoxy isomers), etc.

Formula 1 includes compounds such as those depicted by Formulas 2-24.

Formula 2

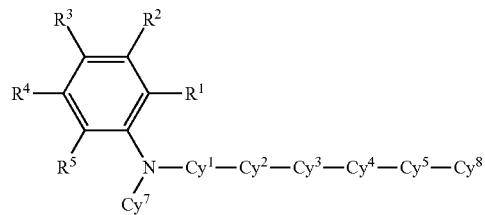

Formula 3

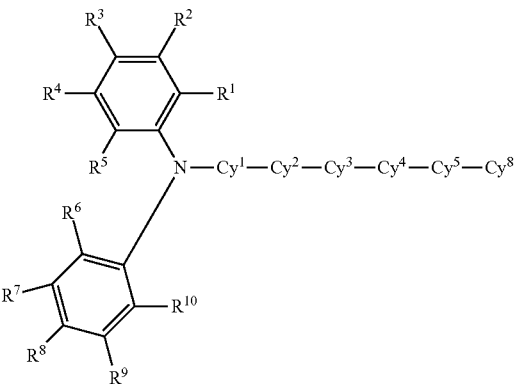

Formula 4

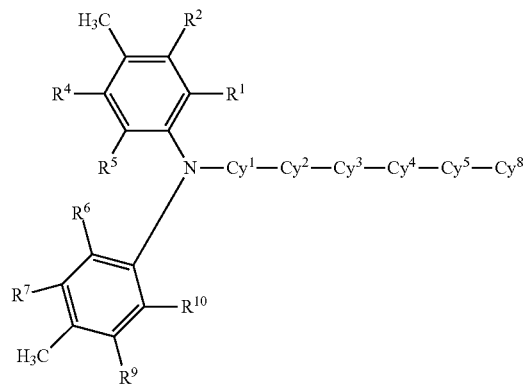

Formula 5

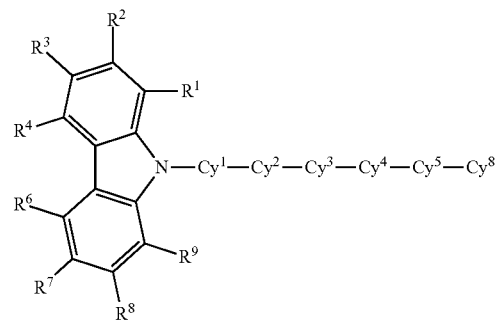

Formula 6
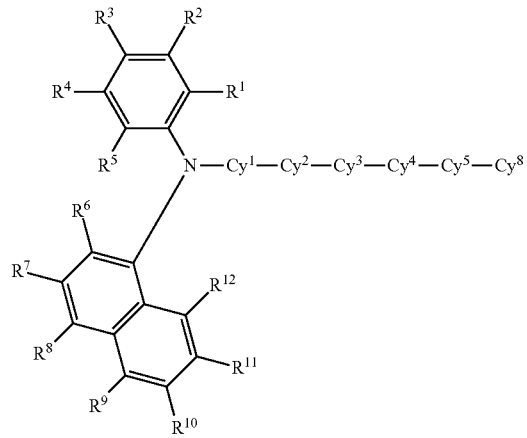
Formula 7
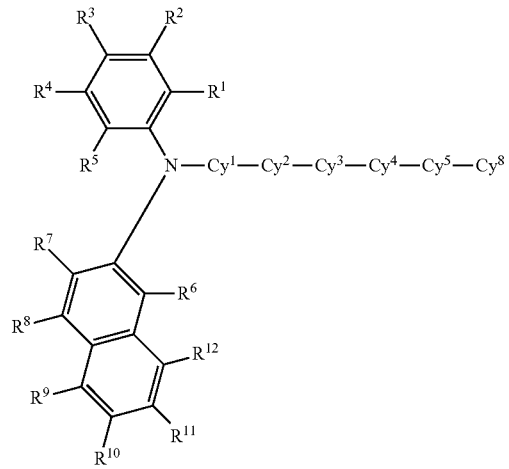
Formula 8
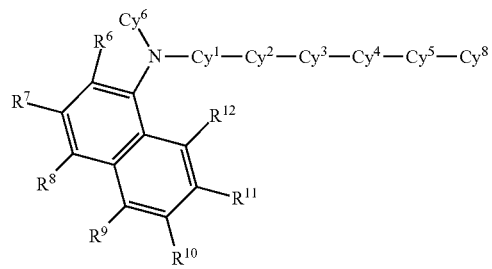
Formula 9
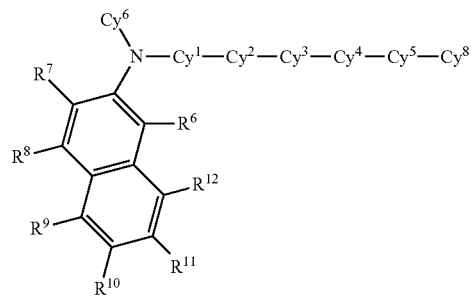
Formula 10
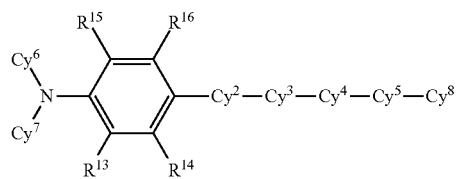
Formula 11
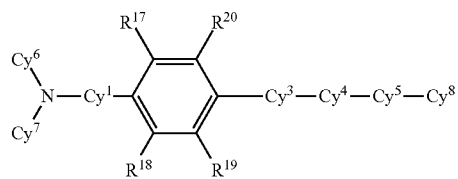
Formula 12
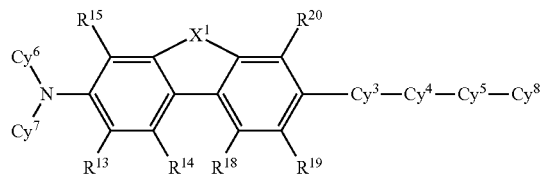
Formula 13
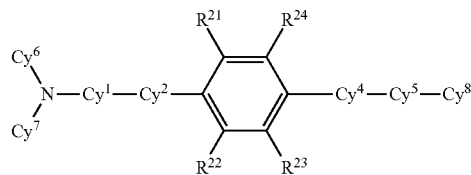
Formula 14
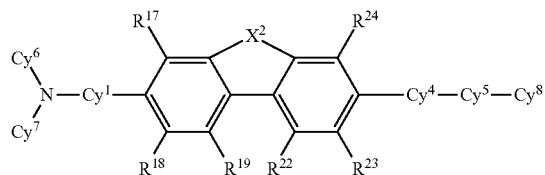
Formula 15
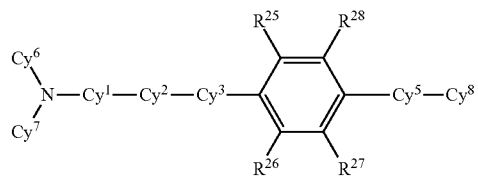
Formula 16
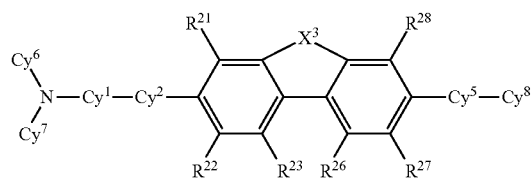
Formula 17
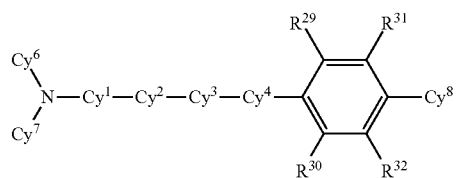

Formula 18
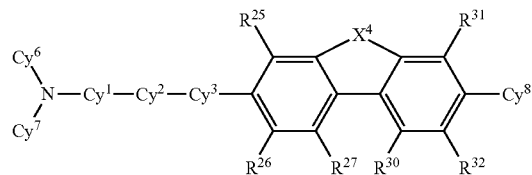
Formula 19
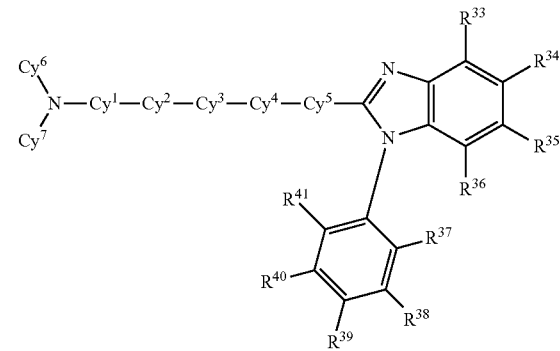
Formula 20
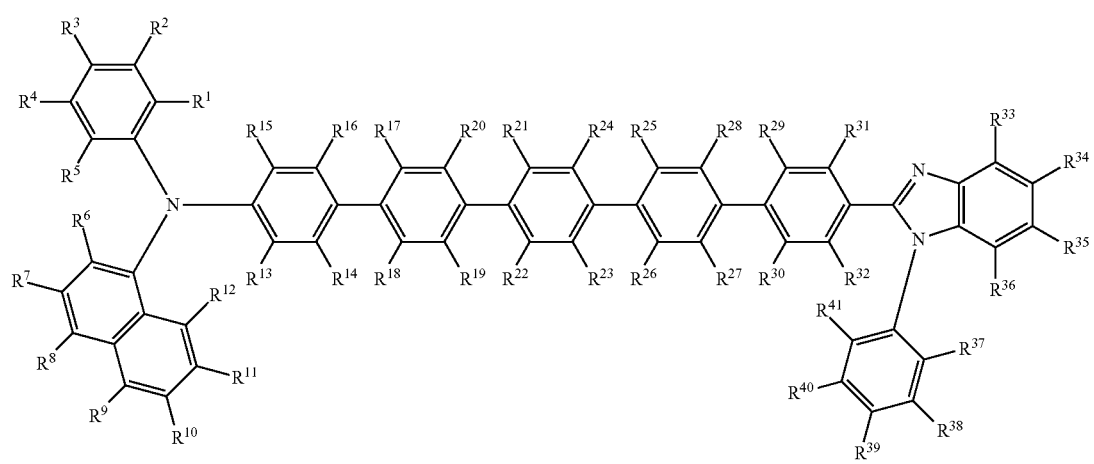
Formula 21
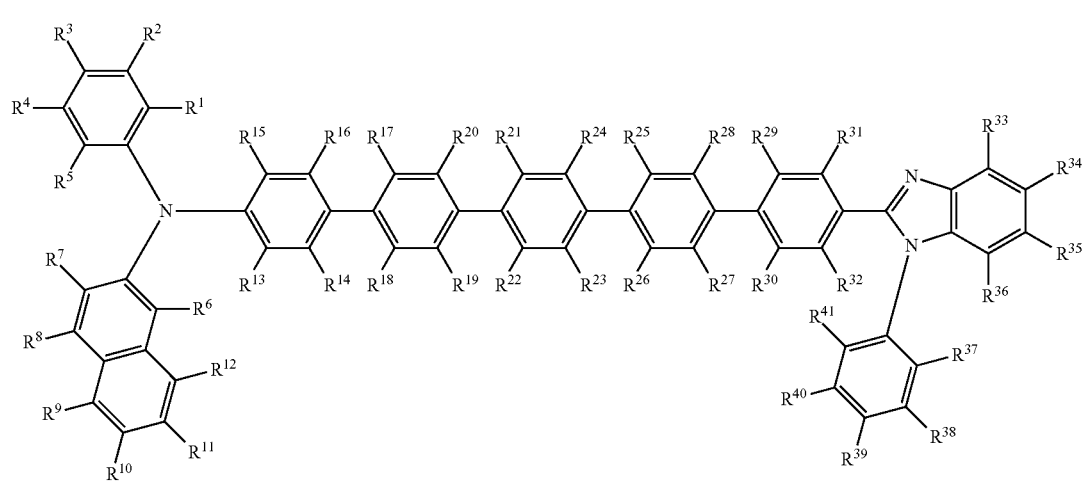

Formula 22

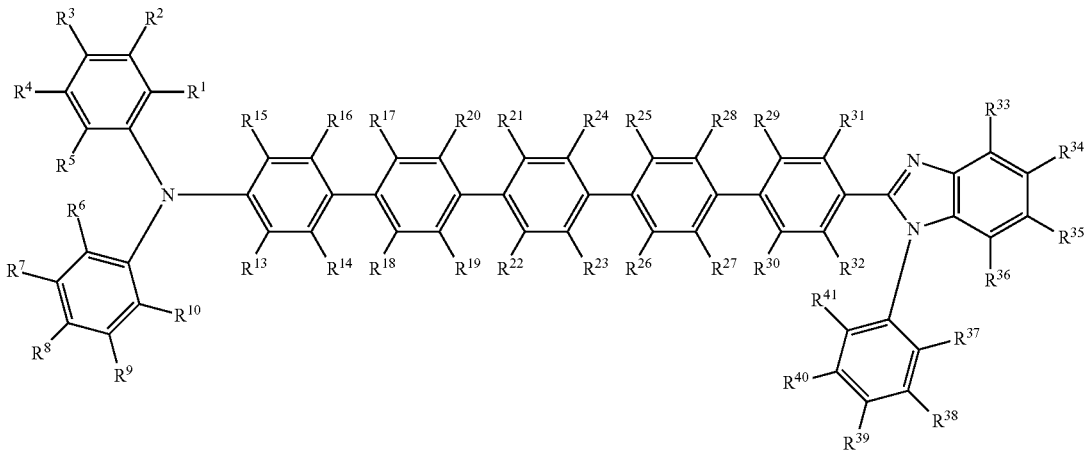

Formula 23

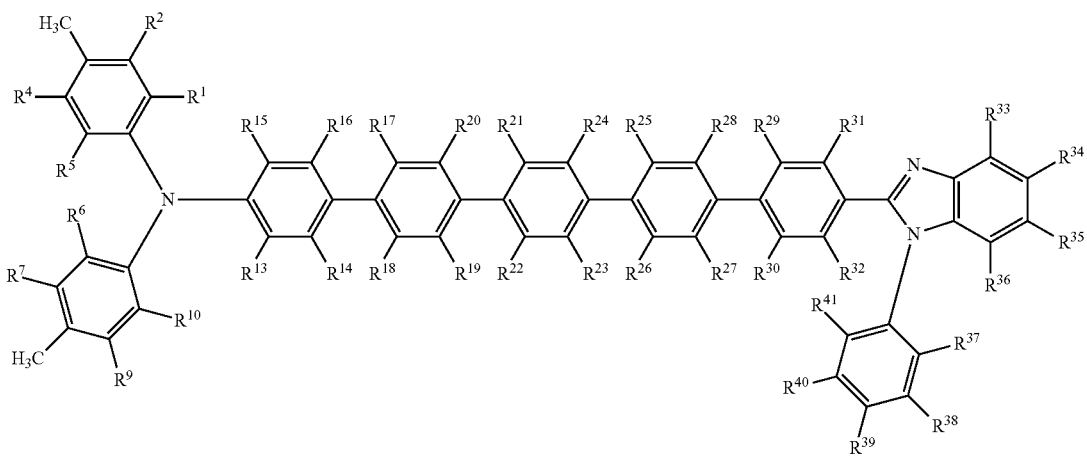

Formula 24

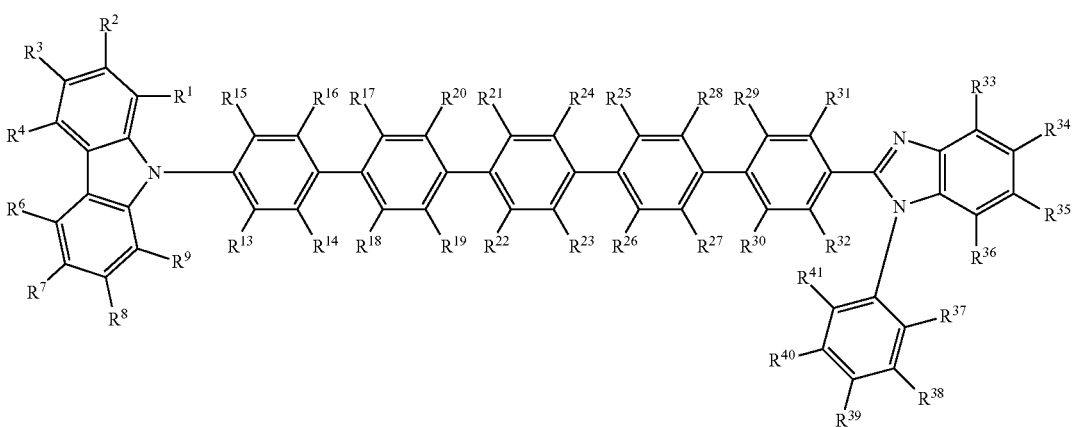

With respect to any relevant formula or structural depiction herein, Cy1, Cy2, Cy3, Cy4, and Cy5 may independently be optionally substituted p-phenylene. Those having ordinary skill in the art will readily recognize that the synthesis of compounds having five adjacent p-phenylene moieties presents considerable technical and synthetic difficulty, with no apparent benefit. Thus, absent the teachings provided herein, the tendency of those having ordinary skill in the art is to avoid such a molecular configuration. In some embodiments, if the p-phenylene is substituted, it may have 1, 2, 3, or 4 substituents. In some embodiments, some or all of the substituents on the p-phenylene may have: from 0 to 10 carbon atoms and from 0 to 10 heteroatoms independently selected from: O, N, S, F, Cl, Br, and I; and/or a molecular weight of 15 g/mol to 500 g/mol. For example, the substituents may be C1-10 alkyl, such as CH3, C2H5, C3H7, cyclic C3H5, C4H9, cyclic C4H7, C5H11, cyclic C5H9, C6H13, cyclic C6H11, etc.; C1-10 alkoxy; halo, such as F, Cl, Br, I; OH; CN; NO2; C1-6 fluoroalkyl, such as CF3, CF2H, C2F5, etc.; a C1-10 ester such as —O2CCH3, —CO2CH3, —O2CC2H5, —CO2C2H5, —O2C-phenyl, —OC2-phenyl, etc.; a C1-10 ketone such as —COCH3, —COC2H5, —COC3H7, —CO-phenyl, etc.; or a C1-10 amine such as NH2, NH(CH3), N(CH3)2, N(CH3)C2H5, etc. In some embodiments, the p-phenylene is optionally substituted with 1 or 2 substituents independently selected from $C_{1-6}$ alkyl and F.

In some embodiments, $Cy^1$ may be:

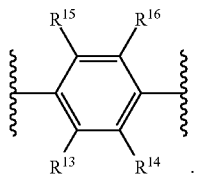

In some embodiments, $Cy^1$ is unsubstituted.

In some embodiments, $Cy^2$ may be:

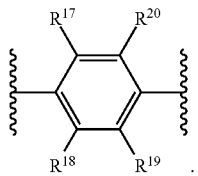

In some embodiments, $Cy^2$ is unsubstituted.

With respect to any relevant formula or structural feature above, such as Formulas 1, 2, 3, 4, 5, 6, 7, 8, 9, 13, 15, 16, 17, 18, and 19, in some embodiments $Cy^1$ and $Cy^2$ are unsubstituted.

In some embodiments, $Cy^1$ and $Cy^2$ may share a linking substituent so that $Cy^1$, $Cy^2$, and the linking substituent form a fused tricyclic ring system. For example, $-Cy^1-Cy^2-$ may be:

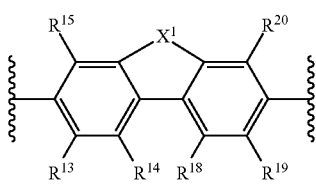

With respect to any relevant formula or structural depiction above, $X^1$ may be any substituent that links $Cy^1$ to $Cy^2$. In some embodiments, the substituent that that links $Cy^1$ to $Cy^2$ may have: from 0 to 15 carbon atoms and from 0 to 10 heteroatoms independently selected from: O, N, S, F, Cl, Br, and I; and/or a molecular weight of 15 g/mol to 500 g/mol.

In some embodiments, $X^1$ may be:

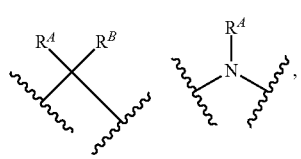

—O—, or —S—.

In some embodiments, $X^1$ may be:

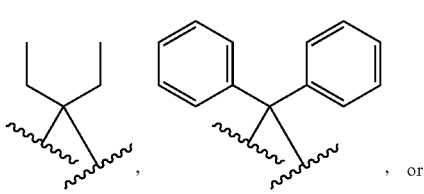

, or

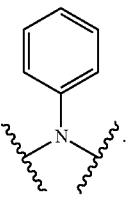

.

In some embodiments, $Cy^3$ may be:

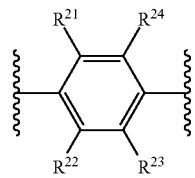

In some embodiments, $Cy^3$ is unsubstituted.

In some embodiments, $Cy^2$ and $Cy^3$ may share a linking substituent so that $Cy^2$, $Cy^3$, and the linking substituent form a fused tricyclic ring system. For example, $-Cy^2-Cy^3-$ may be:

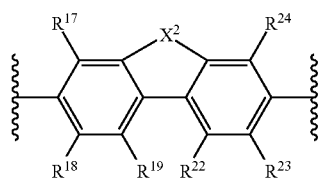

With respect to any relevant formula or structural depiction above, $X^2$ may be any substituent that links $Cy^2$ to $Cy^3$. In some embodiments, the substituent that that links $Cy^2$ to $Cy^3$ may have: from 0 to 15 carbon atoms and from 0 to 10 heteroatoms independently selected from: O, N, S, F, Cl, Br, and I; and/or a molecular weight of 15 g/mol to 500 g/mol.

In some embodiments, $X^2$ may be:

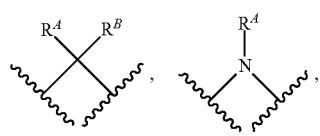

—O—, or —S—.

In some embodiments, $X^2$ may be:

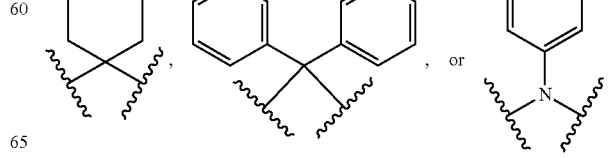

.

In some embodiments, $Cy^4$ may be:

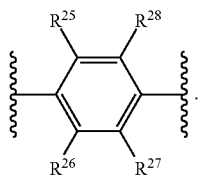

In some embodiments, $Cy^4$ is unsubstituted.

With respect to any relevant formula or structural feature above, such as Formulas 1, 2, 3, 4, 5, 6, 7, 8, 9, 10, 11, 12, 17, and 19, in some embodiments $Cy^3$ and $Cy^4$ are unsubstituted.

In some embodiments, $Cy^3$ and $Cy^4$ may share a linking substituent so that $Cy^3$, $Cy^4$, and the linking substituent form a fused tricyclic ring system. For example, -$Cy^3$-$Cy^4$- may be:

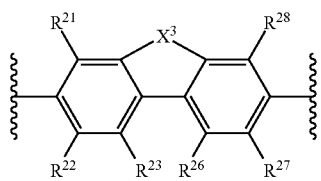

With respect to any relevant formula or structural depiction above, $X^3$ may be any substituent that links $Cy^3$ to $Cy^4$. In some embodiments, the substituent that that links $Cy^3$ to $Cy^4$ may have: from 0 to 15 carbon atoms and from 0 to 10 heteroatoms independently selected from: O, N, S, F, Cl, Br, and I; and/or a molecular weight of 15 g/mol to 500 g/mol.

In some embodiments, $X^3$ may be:

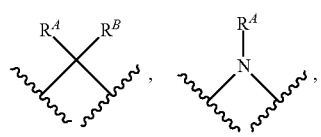

—O—, or —S—.

In some embodiments, $X^3$ may be:

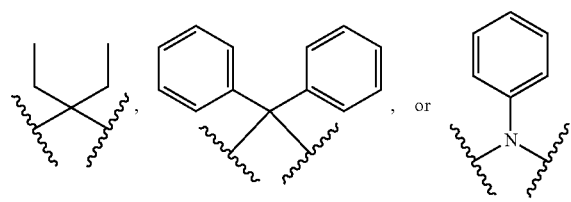

In some embodiments, $Cy^5$ may be:

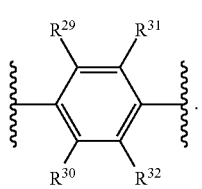

In some embodiments, $Cy^5$ is unsubstituted.

In some embodiments, $Cy^4$ and $Cy^5$ may share a linking substituent so that $Cy^4$, $Cy^5$, and the linking substituent form a fused tricyclic ring system. For example, -$Cy^4$-$Cy^5$- may be:

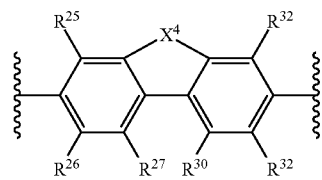

With respect to any relevant formula or structural depiction above, $X^4$ may be any substituent that links $Cy^4$ to $Cy^5$. In some embodiments, the substituent that that links $Cy^4$ to $Cy^5$ may have: from 0 to 15 carbon atoms and from 0 to 10 heteroatoms independently selected from: O, N, S, F, Cl, Br, and I; and/or a molecular weight of 15 g/mol to 500 g/mol.

In some embodiments, $X^4$ may be:

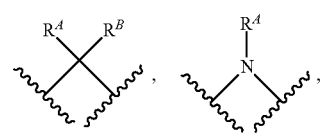

—O—, or —S—.

In some embodiments, $X^4$ may be:

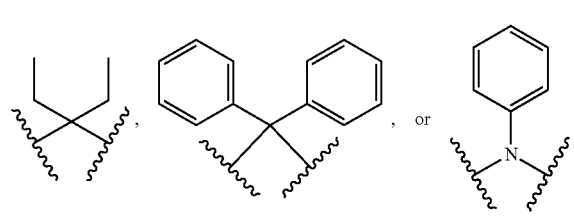

With respect to any relevant formula or structural depiction above, $Cy^6$ may be optionally substituted phenyl. In some embodiments, if the phenyl is substituted, it may have 1, 2, 3, 4, or 5 substituents. Any substituent may be included on the phenyl. In some embodiments, some or all of the substituents on the phenyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, NH-phenyl, etc. In some embodiments, the phenyl is optionally substituted with 1, 2, or 3 substituents independently selected from $C_{1-6}$ alkyl and F. In some embodiments, $Cy^6$ is unsubstituted.

In some embodiments, Cy⁶ may be:

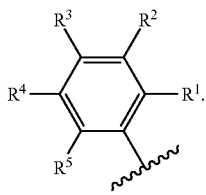

With respect to any relevant formula or structural depiction above, Cy⁷ may be optionally substituted phenyl or optionally substituted naphthalenyl, wherein Cy⁶ and Cy⁷ may optionally link together to form a fused tricyclic ring system comprising N. In some embodiments, if the phenyl is substituted, it may have 1, 2, 3, 4, or 5 substituents. In some embodiments, if the naphthalenyl is substituted, it may have 1, 2, 3, 4, 5, 6, or 7 substituents. Any substituent may be included on the phenyl or the naphthalenyl. In some embodiments, some or all of the substituents on the phenyl or the naphthalenyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the phenyl or the naphthalenyl is optionally substituted with 1, 2, or 3 substituents independently selected from $C_{1-6}$ alkyl and F. In some embodiments, Cy⁷ is unsubstituted.

In some embodiments, Cy⁷ may be:

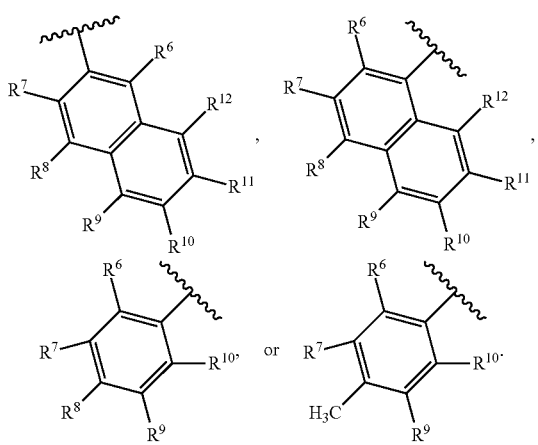

In some embodiments,

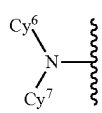

may be:

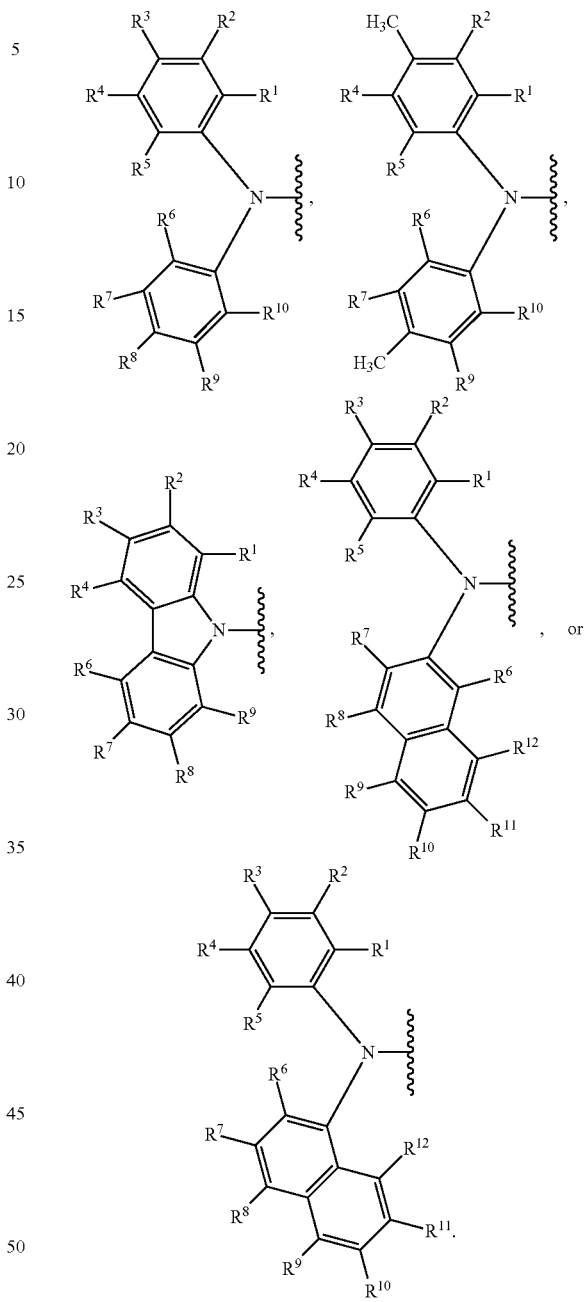

With respect to any relevant formula or structural feature above, such as Formulas 1, 10, 11, 12, 13, 14, 15, 16, 17, 18, and 19, in some embodiments Cy⁶ and Cy⁷ are unsubstituted.

With respect to any relevant formula or structural depiction above, Cy⁸ may be optionally substituted 1-phenyl-1H-benzo[d]imidazol-2-yl. In some embodiments, if the 1-phenyl-1H-benzo[d]imidazol-2-yl is substituted, it may have 1, 2, 3, 4, 5, 6, 7, 8, or 9 substituents. Any substituent may be included. In some embodiments, some or all of the substituents on the phenyl may have: from 0 to 10 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as $—O_2CCH_3$, $—CO_2CH_3$, $—O_2CC_2H_5$, $—CO_2C_2H_5$, $—O_2C$-phenyl, $—CO_2$-phenyl, etc.; a $C_{1-10}$ ketone such as $—COCH_3$, $—COC_2H_5$, $—COC_3H_7$, $—CO$-phenyl, etc.; or a $C_{1-10}$ amine such as $NH_2$, $NH(CH_3)$, $N(CH_3)_2$, $N(CH_3)C_2H_5$, etc. In some embodiments, $Cy^8$ is optionally substituted with 1, 2, or 3 substituents independently selected from $C_{1-6}$ alkyl and F. In some embodiments, $Cy^8$ is unsubstituted.

In some embodiments, $Cy^8$ may be:

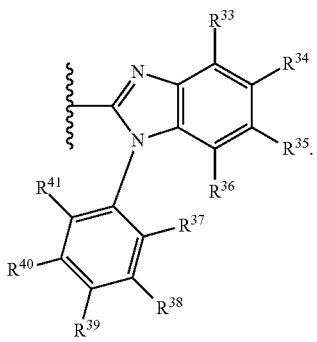

With respect to any relevant formula or structural feature above, such as Formulas 1, 2, 3, 4, 5, 6, 7, 8, 9, 10, 11, 12 13, 14, 15, and 16, in some embodiments $Cy^5$ and $Cy^8$ are unsubstituted.

With respect to any relevant formula or structural depiction herein, each $R^A$ may independently be H; phenyl optionally substituted with 1, 2, 3, 4, or 5 substituents selected from: $C_{1-3}$ alkyl, halo, OH, or $C_{1-3}$ alkoxy; or $C_{1-12}$ alkyl, including: linear or branched alkyl having a formula $C_aH_{2a+1}$, wherein a is 1, 2, 3, 4, 5, 6, 7, 8, 9, 10, 11, or 12, such as: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl having a formula $C_bH_{2b-1}$, wherein b is 3, 4, 5, 6, 7, 8, 9, 10, 11, or 12, such as: $C_3H_5$, $C_4H_7$, $C_5H_9$, $C_6H_{11}$, $C_7H_{13}$, $C_8H_{15}$, $C_9H_{17}$, $C_{10}H_{19}$, etc.

With respect to any relevant formula or structural depiction above, each $R^B$ may independently be H; phenyl optionally substituted with 1, 2, 3, 4, or 5 substituents selected from: $C_{1-3}$ alkyl, halo, OH, or $C_{1-3}$ alkoxy; or $C_{1-12}$ alkyl, including: linear or branched alkyl having a formula $C_aH_{2a+1}$, wherein a is 1, 2, 3, 4, 5, 6, 7, 8, 9, 10, 11, or 12, such as: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl having a formula $C_bH_{2b-1}$, wherein b is 3, 4, 5, 6, 7, 8, 9, 10, 11, or 12, such as: $C_3H_5$, $C_4H_7$, $C_5H_9$, $C_6H_{11}$, $C_7H_{13}$, $C_8H_{15}$, $C_9H_{17}$, $C_{10}H_{19}$, etc.

With respect to any relevant formula or structural depiction above, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, and $R^{41}$ ("$R^{1-41}$") may independently be H or any substituent, such as a substituent having from 0 to 6 carbon atoms and from 0 to 5 heteroatoms independently selected from: O, N, S, F, Cl, Br, and I, wherein the substituent has a molecular weight of 15 g/mol to 300 g/mol. Some non-limiting examples of any of $R^{1-41}$ may independently include $R^A$, F, Cl, CN, $OR^A$, $CF_3$, $NO_2$, $NR^AR^B$, $COR^A$, $CO_2R^A$, $OCOR^A$, etc. In some embodiments, any of $R^{1-41}$ may independently be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, any of $R^{1-41}$ may independently be H, F, methyl, ethyl, propyl, or isopropyl. In some embodiments, any of $R^{1-41}$ may be H. In some embodiments, any of $R^{1-41}$ may independently be a linking group that is attached to two or more structural features, e.g., any of $R^{1-41}$ may be a linking substituent so that $Cy^1$, $Cy^2$, and the linking substituent form a fused tricyclic ring system as described in greater detail herein.

With respect to any relevant formula or structural feature above, such as Formulas 2, 3, 6, 7, 20, 21, and 22 in some embodiments $R^1$, $R^2$, $R^3$, $R^4$, and $R^5$ are independently H, F, methyl, ethyl, propyl, or isopropyl. In some embodiments $R^1$, $R^2$, $R^3$, $R^4$, and $R^5$ are H.

With respect to any relevant formula or structural feature above, such as Formulas 4 and 23, in some embodiments $R^1$, $R^2$, $R^4$, and $R^5$ are independently H, F, methyl, ethyl, propyl, or isopropyl. In some embodiments $R^1$, $R^2$, $R^4$, and $R^5$ are H.

With respect to any relevant formula or structural feature above, such as Formulas 6, 7, 8, 9, 20, and 21, in some embodiments $R^6$, $R^7$, $R^8$, $R^9$, $R^{10}$, $R^{11}$, and $R^{12}$ are independently H, F, methyl, ethyl, propyl, or isopropyl. In some embodiments $R^6$, $R^7$, $R^8$, $R^9$, $R^{10}$, $R^{11}$, and $R^{12}$ are H.

With respect to any relevant formula or structural feature above, such as Formulas 6, 7, 20, and 21, in some embodiments, $R^1$, $R^2$, $R^3$, $R^4$, $R^5$, $R^6$, $R^7$, $R^8$, $R^9$, $R^{10}$, $R^{11}$, and $R^{12}$ are independently H, F, methyl, ethyl, propyl, or isopropyl. In some embodiments $R^1$, $R^2$, $R^3$, $R^4$, $R^5$, $R^6$, $R^7$, $R^8$, $R^9$, $R^{10}$, $R^{11}$, and $R^{12}$ are H.

With respect to any relevant formula or structural feature above, such as Formulas 3 and 22, in some embodiments $R^1$, $R^2$, $R^3$, $R^4$, $R^6$, $R^7$, $R^8$, $R^9$, and $R^{10}$ are independently H, F, methyl, ethyl, propyl, or isopropyl. In some embodiments $R^1$, $R^2$, $R^3$, $R^4$, $R^6$, $R^7$, $R^8$, $R^9$, and $R^{10}$ are H.

With respect to any relevant formula or structural feature above, such as Formulas 10, 20, 21, 22, 23, and 24, in some embodiments $R^{13}$, $R^{14}$, $R^{15}$, and $R^{16}$ are independently H, F, methyl, ethyl, propyl, or isopropyl. In some embodiments $R^{13}$, $R^{14}$, $R^{15}$, and $R^{16}$ are H.

With respect to any relevant formula or structural feature above, such as Formulas 11, 20, 21, 22, 23, and 24, in some embodiments $R^{17}$, $R^{18}$, $R^{19}$, and $R^{20}$ are independently H, F, methyl, ethyl, propyl, or isopropyl. In some embodiments $R^{17}$, $R^{18}$, $R^{19}$, and $R^{20}$ are H With respect to any relevant formula or structural feature above, such as Formulas 13, 20, 21, 22, 23, and 24, in some embodiments, $R^{21}$, $R^{22}$, $R^{23}$, and $R^{24}$ are independently H, F, methyl, ethyl, propyl, or isopropyl. In some embodiments $R^{21}$, $R^{22}$, $R^{23}$, and $R^{24}$ are H.

With respect to any relevant formula or structural feature above, such as Formulas 15, 20, 21, 22, 23, and 24, in some embodiments $R^{25}$, $R^{26}$, $R^{27}$, and $R^{28}$ are independently H, F, methyl, ethyl, propyl, or isopropyl. In some embodiments $R^{25}$, $R^{26}$, $R^{27}$, and $R^{28}$ are H.

With respect to any relevant formula or structural feature above, such as Formulas 17, 20, 21, 22, 23, and 24, in some embodiments $R^{29}$, $R^{30}$, $R^{31}$, and $R^{32}$ are independently H, F, methyl, ethyl, propyl, or isopropyl. In some embodiments $R^{29}$, $R^{30}$, $R^{31}$, and $R^{32}$ are H.

With respect to any relevant formula or structural feature above, such as Formulas 19, 20, 21, 22, 23, and 24, in some embodiments $R^{33}$, $R^{34}$, $R^{35}$, $R^{36}$, $R^{37}$, $R^{38}$, $R^{39}$, $R^{40}$, and $R^{41}$ are independently H, F, methyl, ethyl, propyl, or isopropyl. In some embodiments $R^{33}$, $R^{34}$, $R^{35}$, $R^{36}$, $R^{37}$, $R^{38}$, $R^{39}$, $R^{40}$, and $R^{41}$ are H.

Some embodiments may include one of the compounds below:

In some embodiments, an organic light-emitting device comprises a subject compound. For example, light-emitting layer comprising a subject compound may is disposed between an anode and a cathode. The device is configured so that electrons can be transferred from the cathode to the

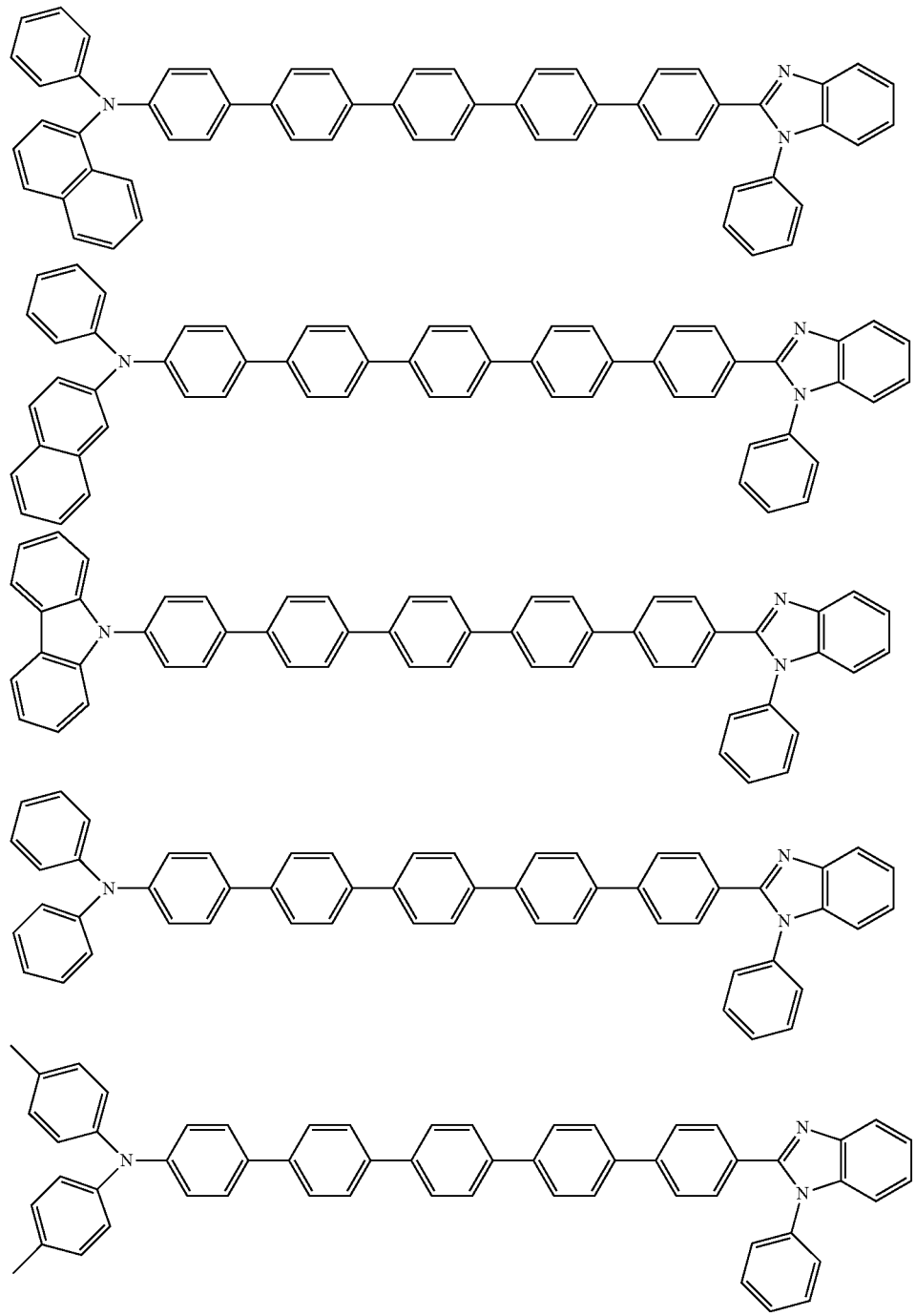

Some embodiments include a composition comprising a compound of any one of Formulas 1-24 or any specific compound depicted or named herein (hereinafter referred to as "a subject compound"). A composition comprising a subject compound may further comprise a fluorescent compound or a phosphorescent compound, and may be useful for light emission in devices such as organic light-emitting devices.

light-emitting layer and holes can be transferred from the anode to the light-emitting layer.

The subject compounds may have high photostability and thermal stability in organic light-emitting devices. The subject compounds may also have well balanced hole and electron injection rates and mobilities. This may provide OLED devices with high efficiencies and/or long lifetimes. The subject compounds may also form amorphous solids, which may make the compounds easy to form into films.

The anode may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). In some embodiments, the anode layer can have a thickness in the range of about 1 nm to about 1000 nm.

A cathode may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, a light-emitting layer may comprise a light-emitting component and a subject compound as a host. The amount of the host in a light-emitting layer may vary. In one embodiment, the amount of a host in a light-emitting layer is in the range of from about 1% to about 99.9% by weight of the light-emitting layer. In another embodiment, the amount of a host in a light-emitting layer is in the range of from about 90% to about 99% by weight of the light-emitting layer. In another embodiment, the amount of a host in a light-emitting layer is about 97% by weight of the light-emitting layer. In some embodiments, the mass of the light-emitting component is about 0.1% to about 10%, about 1% to about 5%, or about 3% of the mass of the light-emitting layer. The light-emitting component may be a fluorescent and/or a phosphorescent compound.

A light-emitting component may comprise an iridium coordination compound such as: bis-{2-[3,5-bis(trifluoromethyl)phenyl]pyridinato-N,C2'}iridium(III)-picolinate; bis(2-[4,6-difluorophenyl]pyridinato-N,C2')iridium(III) picolinate; bis(2-[4,6-difluorophenyl]pyridinato-N,C2')iridium (acetylacetonate); Iridium (III) bis(4,6-difluorophenylpyridinato)-3-(trifluoromethyl)-5-(pyridine-2-yl)-1,2,4-triazolate; Iridium (III) bis(4,6-difluorophenylpyridinato)-5-(pyridine-2-yl)-1H-tetrazolate; bis[2-(4,6-difluorophenyl)pyridinato-N,C$^{2'}$]iridium(III) tetra (1-pyrazolyl)borate; Bis[2-(2'-benzothienyl)-pyridinato-N, C3']iridium(III)(acetylacetonate); Bis[(2-phenylquinolyl)-N,C2']iridium(III) (acetylacetonate); Bis[(1-phenylisoquinolinato-N,C2')]iridium(III) (acetylacetonate); Bis[(dibenzo[f,h]quinoxalino-N,C2')iridium(III)(acetylacetonate); Tris(2,5-bis-2'-(9',9'-dihexylfluorene)pyridine)iridium(III); Tris[1-phenylisoquinolinato-N,C2']iridium(III); Tris-[2-(2'-benzothienyl)-pyridinato-N,C3']iridium(III); Tris [1-thiophen-2-ylisoquinolinato-N,C3']iridium(III); Tris[1-(9,9-dimethyl-9H-fluoren-2-yl)isoquinolinato-(N,C3')iridium (III)); Bis(2-phenylpyridinato-N,C2')iridium(III) (acetylacetonate) [Ir(ppy)$_2$(acac)]; Bis(2-(4-tolyl)pyridinato-N,C2')iridium(III)(acetylacetonate) [Ir(mppy)$_2$(acac)]; Bis (2-(4-tert-butyl)pyridinato-N,C2')iridium(III) (acetylacetonate) [Ir(t-Buppy)$_2$(acac)]; Tris(2-phenylpyridinato-N,C2')iridium(III) [Ir(ppy)$_3$]; Bis(2-phenyloxazolinato-N,C2')iridium(III) (acetylacetonate) [Ir (op)$_2$(acac)]; Tris(2-(4-tolyl)pyridinato-N,C2')iridium(III) [Ir(mppy)$_3$]; Bis[2-phenylbenzothiazolato-N, C2']iridium (III)(acetylacetonate); Bis[2-(4-tert-butylphenyl)benzothiazolato-N,C2']iridium(III)(acetylacetonate); Bis[(2-(2'-thienyl)pyridinato-N,C3')]iridium(III) (acetylacetonate); Tris[2-(9.9-dimethylfluoren-2-yl)pyridinato-(N,C3')]iridium(III); Tris[2-(9.9-dimethylfluoren-2-yl)pyridinato-(N,C3')]iridium(III); Bis[5-trifluoromethyl-2-[3-(N-phenylcarbzolyl) pyridinato-N,C2']iridium(III)(acetylacetonate); (2-PhPyCz)$_2$Ir(III)(acac); etc.

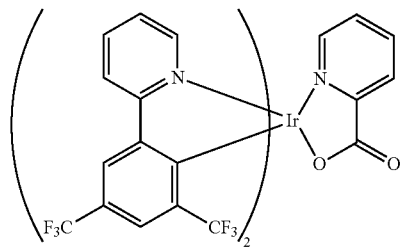

bis-{2-[3,5-bis(trifluoromethyl)phenyl]pyridinato-N, C2'}iridium(III)-picolinate
(Ir(CF$_3$ppy)$_2$(Pic)

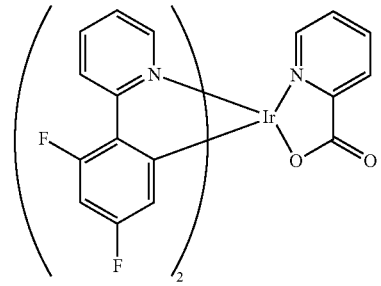

bis(2-[4,6-difluorophenyl]pyridinato-N, C2')iridium (III) picolinate [FIrPic]

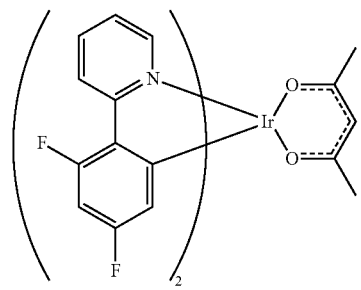

bis(2-[4,6-difluorophenyl]pyridinato-N, C2')iridium(acetylacetonate) [FIr(acac)]

-continued
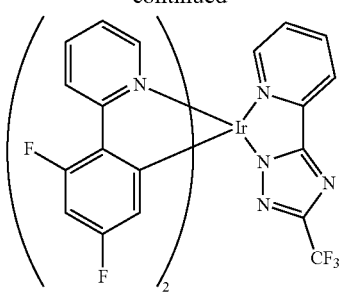
Iridium (III) bis(4,6-difluorophenylpyridinato)-
3-(trifluoromethyl)-5-(pyridine-2-yl)-1,2,4-
triazolate (FIrtaz)
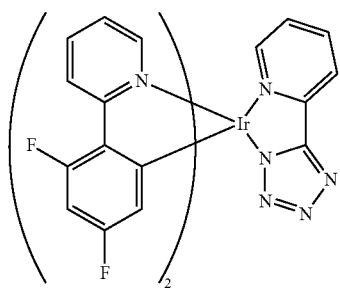
Iridium (III) bis(4,6-
difluorophenylpyridinato)-5-(pyridine-2-yl)-
1H-tetrazolate (FIrN4)
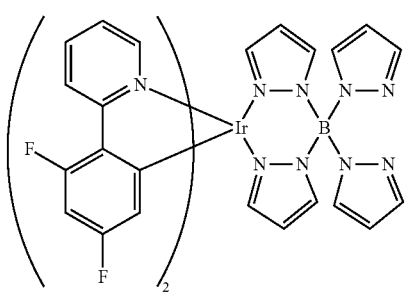
bis[2-(4,6-difluorophenyl)pyridinato-
N, C$^{2'}$]iridium(III)tetra(1-pyrazolyl)borate (Fir6)
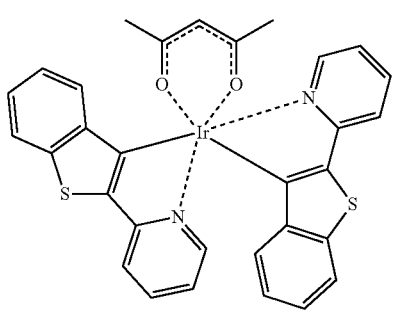
Ir(btp)$_2$(acac) 1
-continued
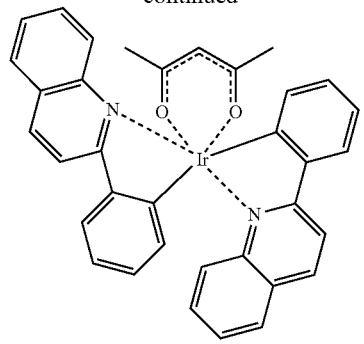
Ir(pq)$_2$(acac) 2
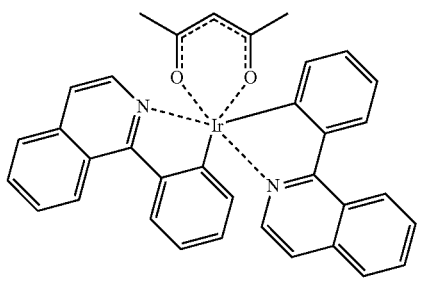
Ir(piq)$_2$(acac) 3
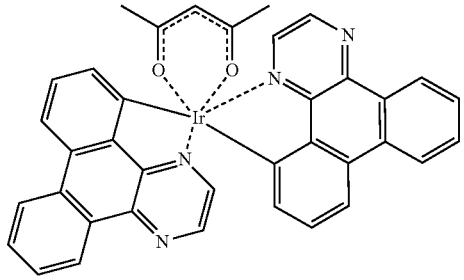
Ir(DBQ)$_2$(acac) 4
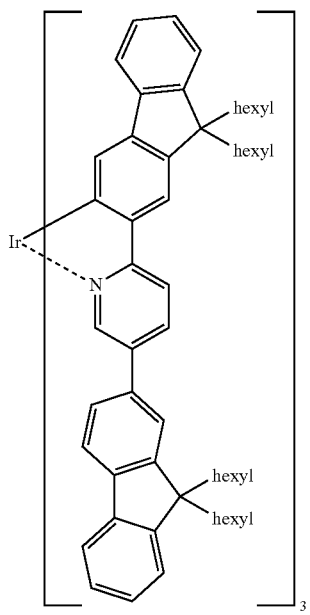
Ir(HFP)$_3$ 5

-continued

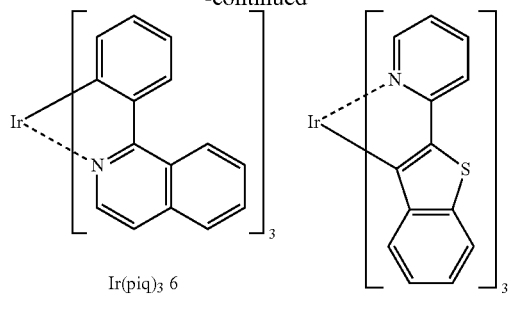

Ir(piq)₃ 6

Ir(btp)₃ 7

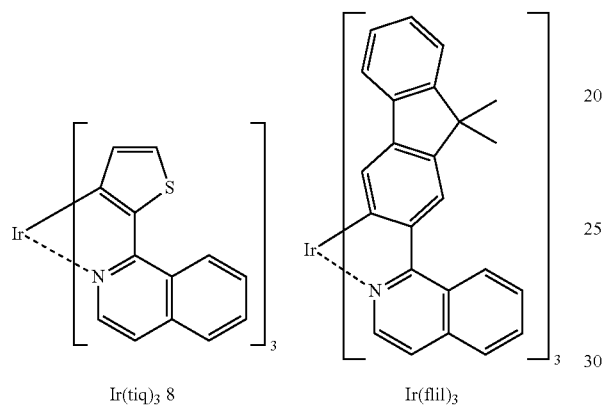

Ir(tiq)₃ 8

Ir(flil)₃

1. (Btp)₂Ir(III)(acac); Bis[2-(2'-benzothienyl)-pyridinato-N, C3'] iridium (III) (acetylacetonate)
2. (Pq)₂Ir(III)(acac); Bis[2-phenylquinolyl-N, C2']iridium (III) (acetylacetonate)
3. (Piq)₂Ir(III)(acac); Bis[(1-phenylisoquinolinato-N, C2')]iridium (III) (acetylacetonate)
4. (DBQ)₂Ir(acac); Bis[(dibenzo[f, h]quinoxalino-N, C2')iridium (III)(acetylacetonate)
5. [Ir(HFP)₃], Tris(2,5-bis-2'-(9',9'-dihexylfluorene)pyridine)iridium (III)
6. Ir(piq)₃; Tris[1-phenylisoquinolinato-N, C2']iridium (III)
7. Ir(btp)₃; Tris-[2-(2'-benzothienyl)-pyridinato-N, C3'] iridium (III)
8. Ir(tiq)₃, Tris[1-thiophen-2-ylisoquinolinato-N, C3']iridium (III)
9. Ir(fliq)₃; Tris[1-(9,9-dimethyl-9H-fluoren-2-yl)isoquinolinato-(N, C3)iridium (III))

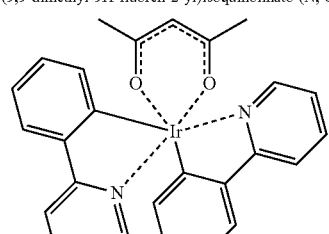

Ir(ppy)₂(acac)

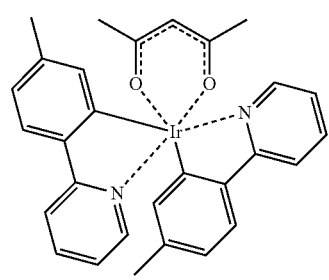

Ir(mppy)₂(acac)

-continued

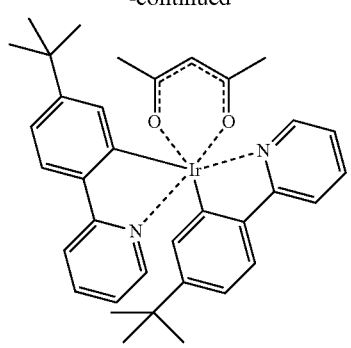

Ir(t-Buppy)₂(acac)

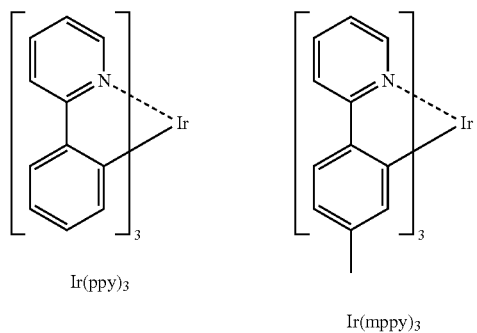

Ir(ppy)₃

Ir(mppy)₃

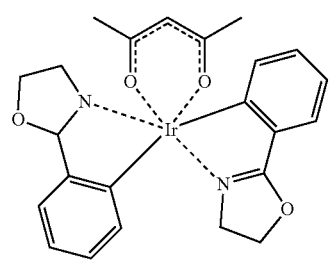

Ir(op)₂(acac)

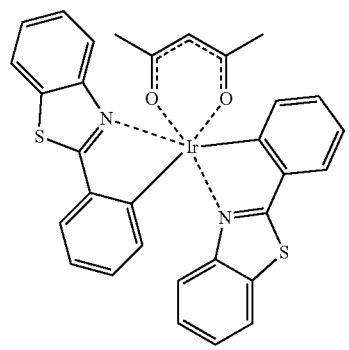

(bt)₂Ir(III)(acac)
Bis[2-phenylbenzothiazolato-N, C2'] iridium (III)(acetylacetonate)

29
-continued

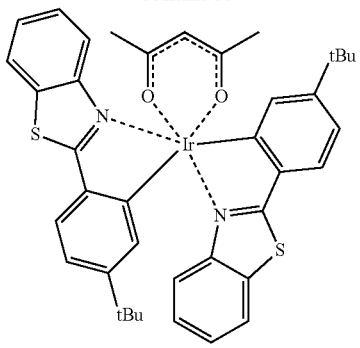

(t-Bt)₂Ir(III)(acac)
Bis[2-(4-tert-
butylphenyl)benzothiazolato-
N, C2']iridium(III)(acetylacetonate)

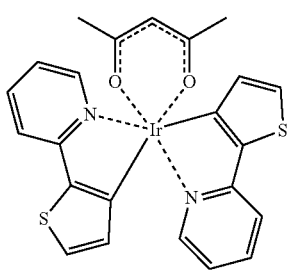

(thp)₂Ir(III)(acac)
Bis[(2-(2'-
thienyl)pyridinato-
N, C3')]iridium (III)
(acetylacetonate)

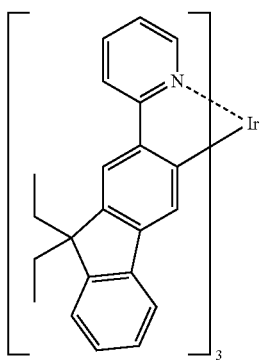

[Ir(Flpy)₃]
Tris[2-(9,9-
dimethylfluoren-2-
yl)pyridinato-
(N, C3')]iridium (III)

30
-continued

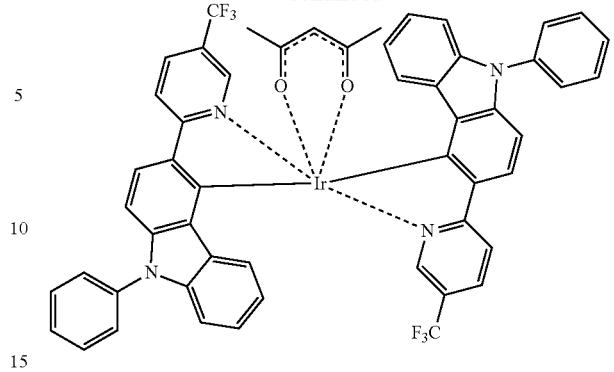

(Cz—CF₃)Ir(III)(acac)
Bis[5-trifluoromethyl-2-[3-(N-
phenylcarbzolyl)pyridinato-
N, C2']iridium(III)(acetylacetonate)

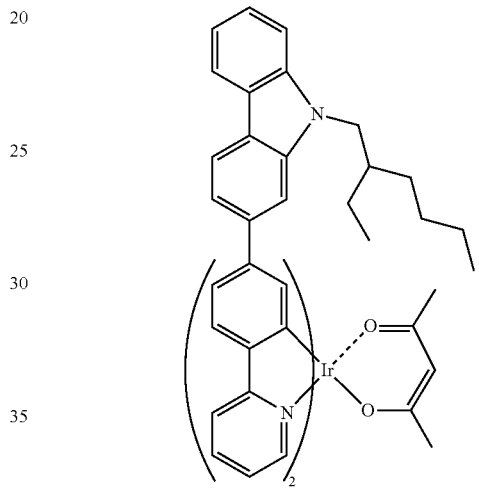

(2-PhPyCz)₂Ir(III)(acac)

The thickness of a light-emitting layer may vary. In one embodiment, a light-emitting layer has a thickness in the range of from about 1 nm to about 150 nm or about 200 nm.

Some embodiments may have a structure as represented schematically by FIG. 1. A light-emitting layer 20 is disposed between an anode 5 and cathode 35. An optional electron-transport layer 30 may be disposed between the light-emitting layer 20 and the cathode 35. An optional hole-injection layer 10 may be disposed between the light-emitting layer 20 and the anode 5, and an optional hole-transport layer 15 may be disposed between the hole-injecting layer 10 and the light-emitting layer 20.

A hole-transport layer may comprise at least one hole-transport material. Hole-transport materials may include, but are not limited to, an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA);

N,N'-bis(3-methylphenyl)N,N'-diphenyl-[1,1'-biphenyl]-4,4'-diamine (TPD); 4,4'-bis[N-(naphthalenyl)-N-phenyl-amino]biphenyl (α-NPD); 4,4',4''-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N''-1,3,5-tricarbazoloylbenzene (tCP); N,N'-bis(4-butylphenyl)-N,N'-bis(phenyl)benzidine; or the like.

A hole-injecting layer may comprise any suitable hole-injecting material. Examples of suitable hole-injecting material(s) include, but are not limited to, an optionally substituted compound selected from the following: molybdenum oxide ($MoO_3$), a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl)benzidine), a triphenyl amine or phenylenediamine derivative such as N,N'-bis(4-methylphenyl)-N,N'-bis(phenyl)-1,4-phenylenediamine, 4,4',4''-tris(N-(naphthalen-2-yl)-N-phenylamino)triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), and a phthalocyanine metal complex derivative such as phthalocyanine copper.

An electron-transport layer may comprise at least one electron-transport material. Examples of electron-transport materials may include, but are not limited to, 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthalenyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthalenyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron-transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron injecting layer (EIL) between the cathode and the light-emitting layer, a hole-blocking layer (HBL) between the anode and the light-emitting layer, and/or an exciton-blocking layer (EBL) between the light-emitting layer and the anode and/or the cathode. In addition to separate layers, some of these materials may be combined into a single layer.

In some embodiments, the light-emitting device can include an electron-injecting layer between the cathode layer and the light-emitting layer. Examples of suitable material(s) that can be included in the electron injecting layer include but are not limited to, an optionally substituted compound selected from the following: lithium fluoride (LiF), aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injecting layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap of the material(s) that comprise exciton-blocking layer is large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthalenyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

Light-emitting devices comprising a subject compound can be fabricated using techniques known in the art, as informed by the guidance provided herein. For example, a glass substrate can be coated with a high work functioning metal such as ITO which can act as an anode. After patterning the anode layer, a light-emitting layer comprising a light-emitting component, can be deposited on the anode. In some embodiments, additional optional layers such as a hole-transport layer, a hole-injecting layer, and/or an exciton-blocking layer may be deposited between the light-emitting layer and the anode, by methods such as vapor deposition, sputtering, or spin coating. The cathode layer, comprising a low work functioning metal (e.g., Mg:Ag), can then be deposited on the light-emitting layer, e.g., by vapor deposition, sputtering, or spin coating. In some embodiments, additional optional layers such as an electron-transport layer, an electron-injection layer, and/or an exciton-blocking layer, can be added to the device using suitable techniques such as vapor deposition, sputtering, or spin coating.

In some embodiments, a device comprising the subject compounds can provide a significantly increased device lifetime compared with commercially available compounds. In some embodiments, the devices can provide a T50(h) @ 10000 nit lifetime of at least about 125 hours, 150 hours, 175 hours, 185 hours, and/or 200 hours. In some embodiments, the desired lifetime can be determined by examining the luminescent/emissive decay of the device by measuring the luminescent, e.g., in $cd/m^2$, after applying a constant current of a 106 mA to device (corresponding to about 10000 $cd/m^2$) for a device having an active emissive surface area of about 13.2 $mm^2$.

Synthetic Examples
Example 1.1
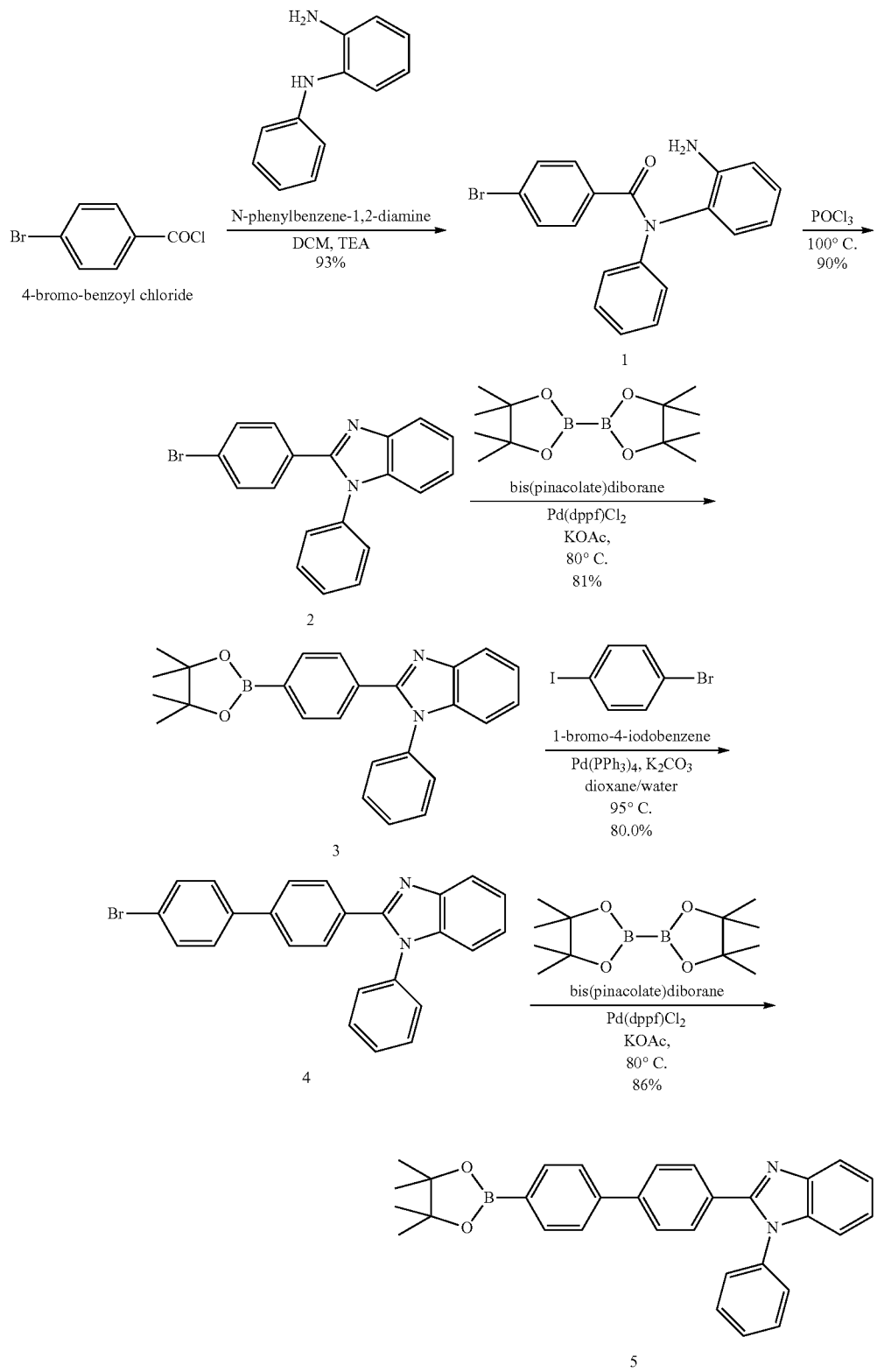

Example 1.1.1

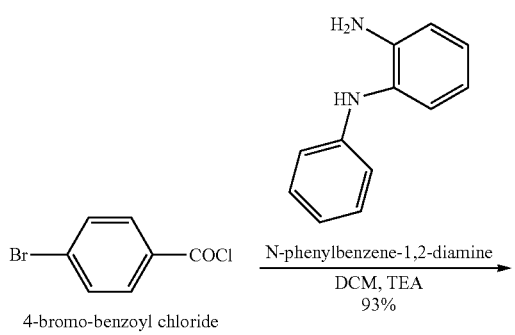

4-Bromo-N-(2-(phenylamino)phenyl)benzamide (1)

To a solution of 4-bromo-benzoyl chloride (11 g, 50 mmol) in anhydrous dichloromethane (DCM) (100 ml), was added N-phenylbenzene-1,2-diamine (10.2 g, 55 mmol), then triethylamine (TEA) (17 ml, 122 mmol) slowly. The whole was stirred at room temperature (RT) overnight. Filtration gave a white solid 1 (6.5 g). The filtrate was worked up with water (300 ml), then extracted with DCM (300 ml) three times. The organic phase was collected and dried over MgSO4, concentrated and recrystallized in DCM/hexanes to give another portion of white solid 1 (10.6 g). Total amount of product 1 is 17.1 g, in 93% yield.

Example 1.1.2

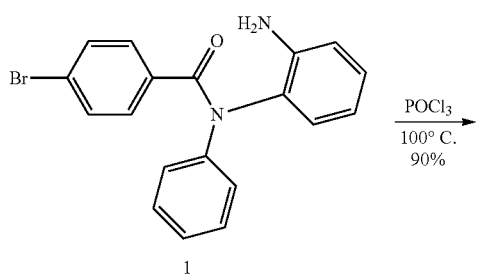

2-(4-bromophenyl)-1-phenyl-1H-benzo[d]imidazole (2)

To a suspension of amide 1 (9.6 g, 26 mmol) in anhydrous 1,4-dioxane (100 mL) was added phosphorus oxychloride (POCl$_3$) (9.2 mL, 100 mmol) slowly. The whole was then heated at 100° C. overnight. After cooling to RT, the mixture was poured into ice (200 g) with stirring. Filtration, followed by recrystallization in DCM/hexanes gave a pale grey solid 2 (8.2 g, in 90% yield).

Example 1.1.3

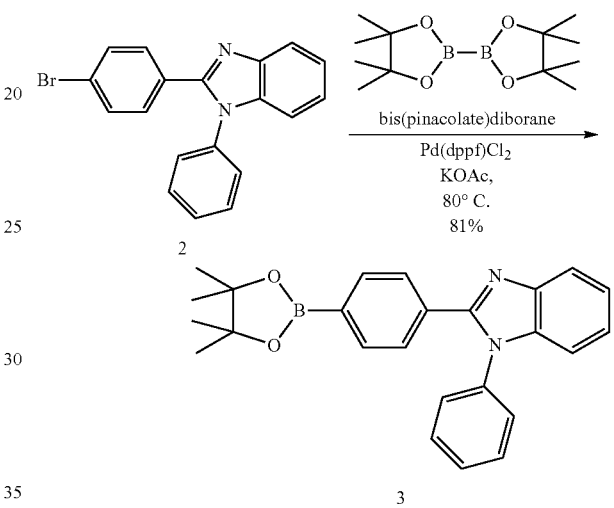

1-phenyl-2-(4-(4,4,5,5-tetramethyl-1,3,2-dioxaborolan-2-yl)phenyl)-1H-benzo[d]imidazole (3)

A mixture of Compound 2 (0.70 g, 2 mmol), bis(pinacolate)diborane (0.533 g, 2.1 mmol), bis(diphenylphosphino)ferrocene]dichloropalladium (Pd(dppf)Cl$_2$) (0.060 g, 0.08 mmol) and anhydrous potassium acetate (KOAc) (0.393 g, 4 mmol) in 1,4-dioxane (20 ml) was heated at 80° C. under argon overnight. After cooling to RT, the whole was diluted with ethyl acetate (80 ml) then filtered. The solution was absorbed on silica gel, then purified by column chromatography (hexanes/ethyl acetate 5:1 to 3:1) to give a white solid 3 (0.64 g, in 81% yield).

Example 1.1.3

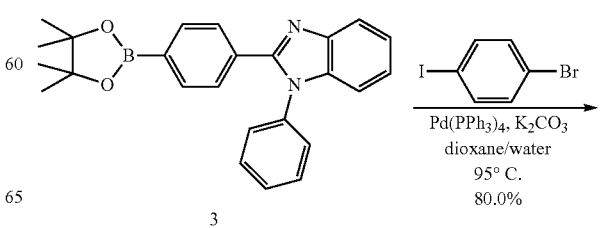

-continued

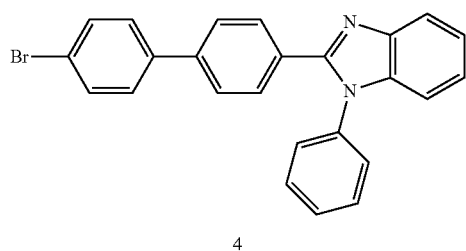

4

2-(4'-bromo-[1,1'-biphenyl]-4-yl)-1-phenyl-1H-benzo[d]imidazole (4)

A mixture of compound 3 (4.01 g, 10.1 mmol), 1-bromo-4-iodobenzene (5.73 g, 20.2 mmol), Pd(PPh$_3$)$_4$ (0.58 g, 0.5 mmol) and potassium carbonate (4.2 g, 30 mmol) in dioxane/water (60 ml/10 ml) was degassed and heated at 95° C. overnight. After being cooled to RT, the mixture was poured into ethyl acetate (250 ml), washed with brine, dried over Na$_2$SO$_4$, then loaded on silica gel, purified by flash column (hexanes to hexanes/ethyl acetate 4:1) to give a light yellow solid washed with methanol and dried in air (3.39 g, in 80% yield).

Example 1.1.4

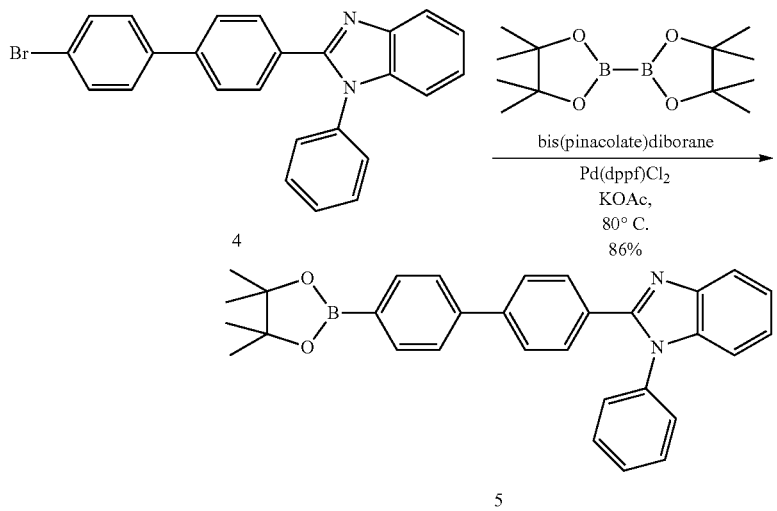

1-phenyl-2-(4'-(4,4,5,5-tetramethyl-1,3,2-dioxaborolan-2-yl)-[1,1'-biphenyl]-4-yl)-1H-benzo[d]imidazole (5)

A mixture of Compound 4 (1.2 g, 2.82 mmol), bis(pinacolate)diborane (0.72 g, 2.82 mmol), bis(diphenylphosphino)ferrocene]dichloropalladium (Pd(dppf)Cl$_2$) (0.10 g, 0.14 mmol) and anhydrous potassium acetate (KOAc) (2.0 g, 20 mmol) in 1,4-dioxane (45 ml) was heated at 80° C. under argon overnight. After cooling to RT, the whole was diluted with ethyl acetate (150 ml) then filtered. The solution was absorbed on silica gel, then purified by column chromatography (hexanes/ethyl acetate 5:1 to 3:1) to give a white solid 5 (1.14 g, in 86% yield).

Example 1.2

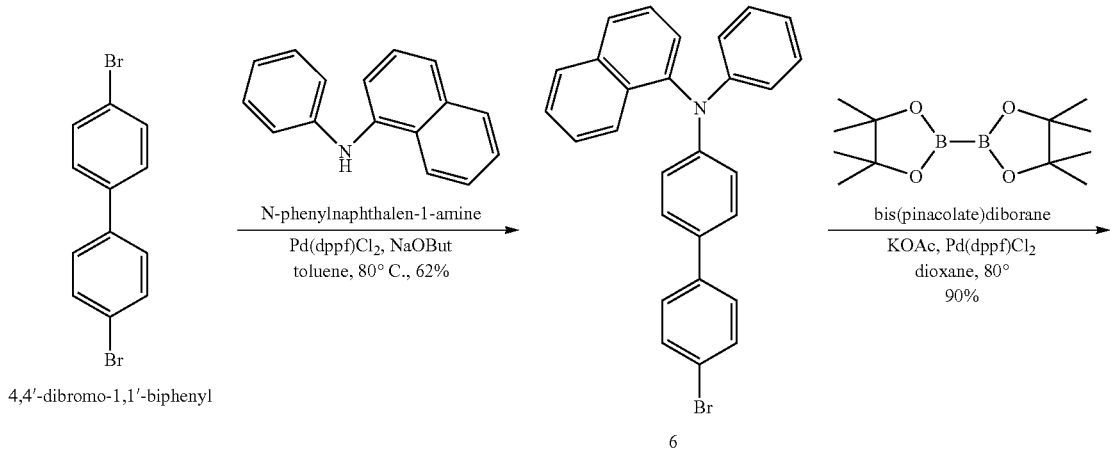

-continued
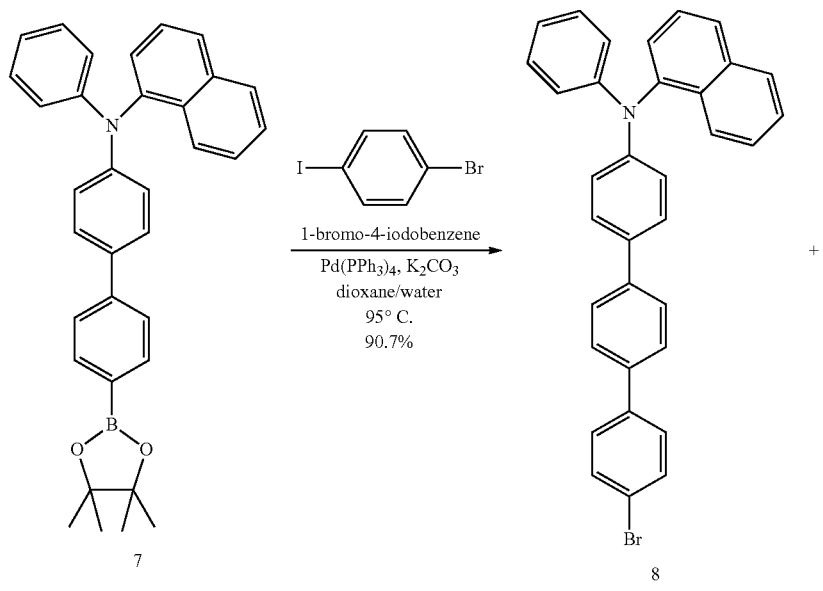
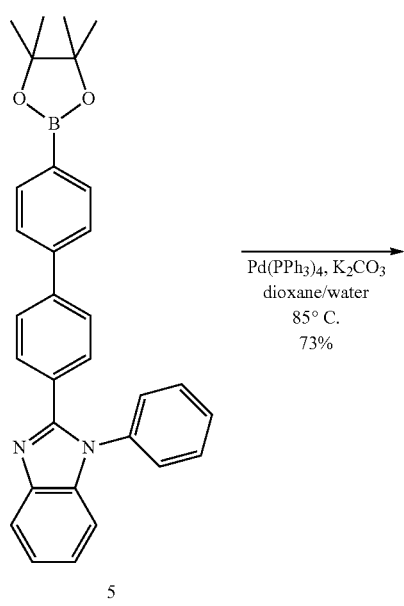
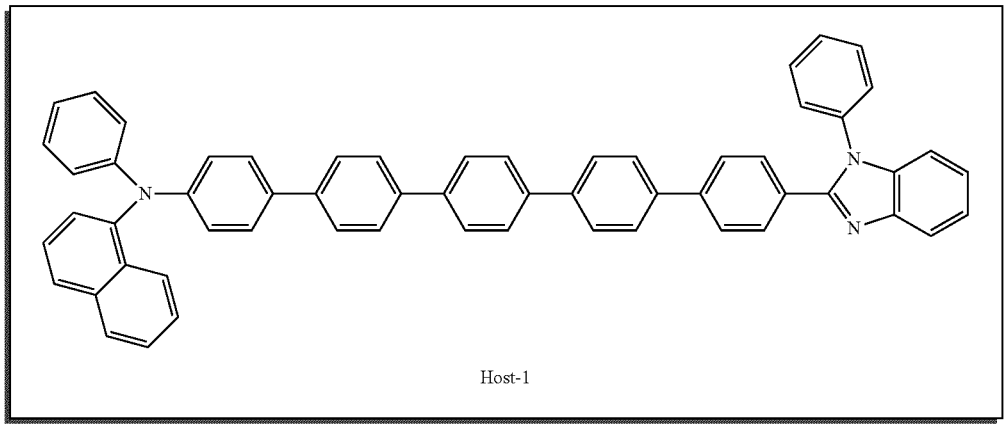
Host-1

Example 1.2.1

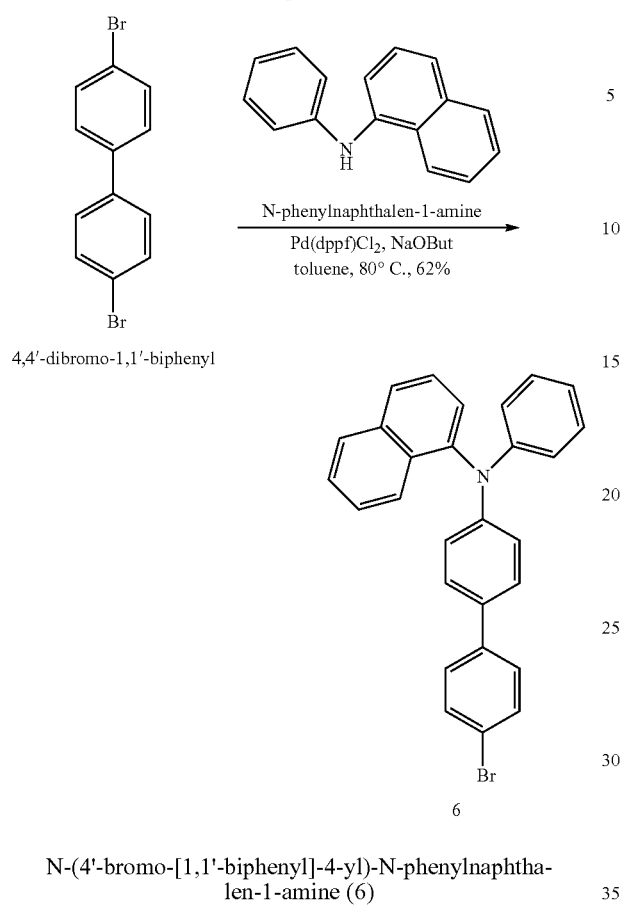

4,4'-dibromo-1,1'-biphenyl

N-(4'-bromo-[1,1'-biphenyl]-4-yl)-N-phenylnaphthalen-1-amine (6)

A mixture of N-phenylnaphthalen-1-amine (4.41 g, 20 mmol), 4,4'-dibromo-1,1'-biphenyl (15 g, 48 mmol), sodium tert-butoxide (4.8 g, 50 mmol) and Pd(dppf)Cl₂ (0.44 g, 0.6 mmol) in anhydrous toluene (100 ml) was degassed and heated at 80° C. for 10 hours. After cooling to RT, the mixture was poured into dichloromethane (400 ml) and stirred for 30 min, then washed with brine (100 ml). The organic is collected and dried over Na₂SO₄, loaded on silica gel, and purified by flash column (hexanes to hexanes/ethyl acetate 90:1) to give a solid which was washed with methanol and dried under air to give a white solid 4 (5.58 g, in 62% yield).

Example 1.2.2

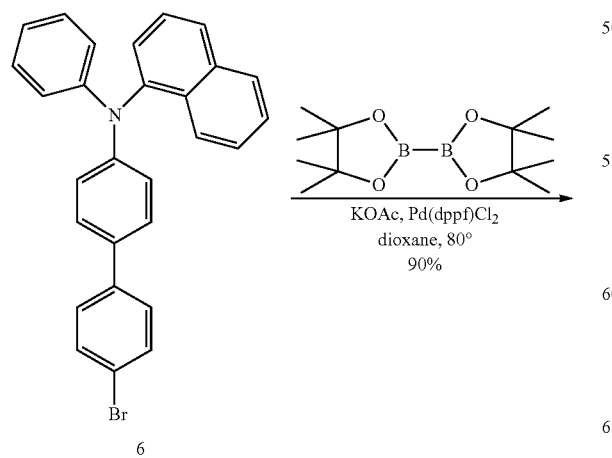

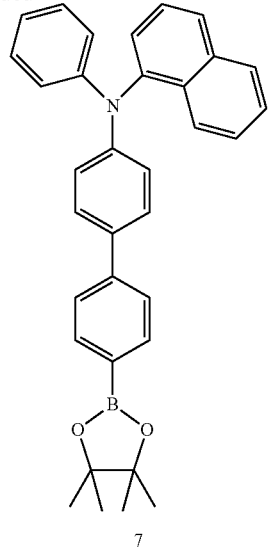

N-phenyl-N-(4'-(4,4,5,5-tetramethyl-1,3,2-dioxaborolan-2-yl)-[1,1'-biphenyl]-4-yl)naphthalen-1-amine (7)

A mixture of Compound 6 (5.5 g, 12.2 mmol), bis(pinacolate)diborane (3.10 g, 12.2 mmol), Pd(dppf)Cl₂ (0.446 mg, 0.6 mmol) and KOAc (5.5 g, 56 mmol) in anhydrous dioxane (60 ml) was degassed and heated at 80° C. overnight. After being cooled to RT, the mixture was poured into ethyl acetate (200 ml), washed with brine (150 ml). The organic solution was dried over Na₂SO₄, loaded on silica gel and purified by flash column (hexanes to hexanes/ethyl acetate 30:1) to collect the major fraction. After removal of solvent, the solid was washed with methanol, filtered and dried in air to give a white solid 7 (5.50 g, in 90% yield).

Example 1.2.3

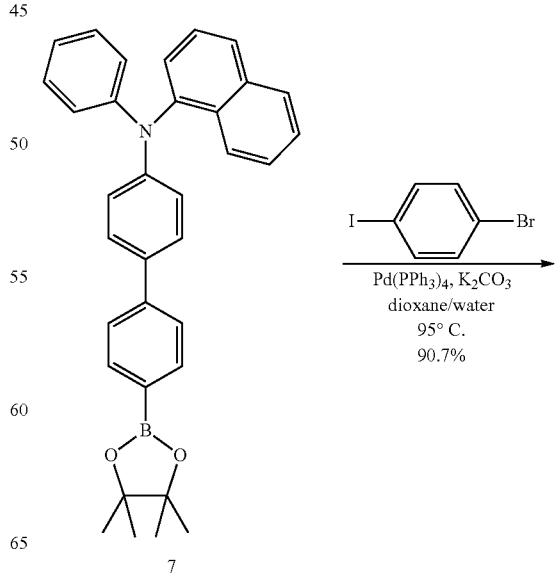

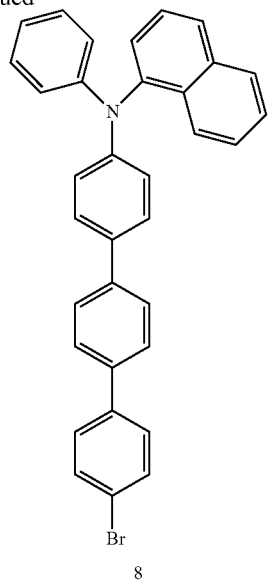

N-(4"-bromo-[1,1':4',1"-terphenyl]-4-yl)-N-phenyl-naphthalen-1-amine (8)

A mixture of compound 7 (4.5 g, 9.0 mmol), 1-bromo-4-iodobenzene (5.12 g, 18 mmol), Pd(PPh$_3$)$_4$ (0.52 g, 0.45 mmol) and potassium carbonate (4.436 g, 32 mmol) in dioxane/water (150 ml/30 ml) was degassed and heated at 95° C. overnight. After being cooled to RT, the mixture was poured into dichloromethane (300 ml), washed with brine, dried over Na$_2$SO$_4$, then loaded on silica gel, purified by flash column (hexanes to hexanes/ethyl acetate 20:1) to give a light yellow solid 8 (4.30 g, in 90.7 yield).

Example 1.2.4

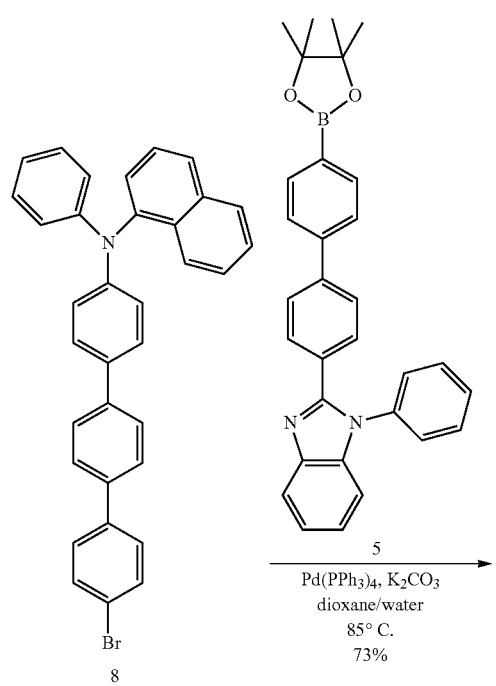

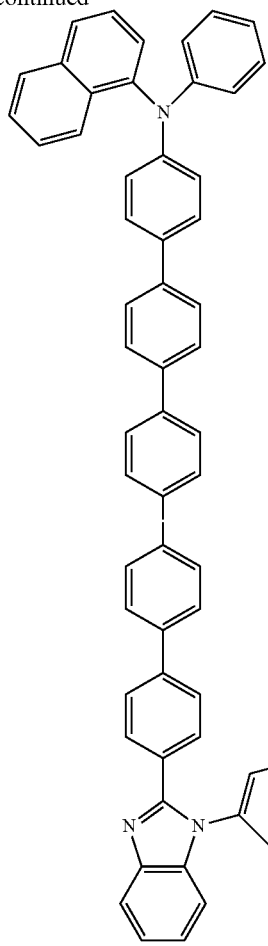

Host-1:

A mixture of compound 8 (1.50 g, 2.47 mmol), compound 5 (1.11 g, 2.35 mmol), Pd(PPh$_3$)$_4$ (0.16 g, 0.14 mmol) and potassium carbonate (1.38 g, 10 mmol) in dioxane/water (60 ml/10 ml) was degassed and heated at 85° C. for 18 hours. After being cooled to RT, the mixture was filtered. The solid and the filtrate were collected separately. The solid from the first filtration was redissolved in dichloromethane (100 ml), loaded on silica gel, and purified by flash column (dichloromethane to dichloromethane/ethyl acetate 9:1) to collect the desired fraction, concentrated. The white precipitate was filtered and dried in air to give a light yellow solid, Host-1 (1.35 g). The overall yield is 73%. LCMS data: calcd for C$_{59}$H$_{42}$N$_3$ (M+H): 792.3. found m/e=792.

8-2. Example of OLED Device Configuration and Performance

Example 2.1

(Device-A)—Fabrication of Light-Emitting Device

A device (Device A) was fabricated in a manner similar to the following. The ITO substrates having sheet resistance of about 14 ohm/sq were cleaned ultrasonically and sequentially in detergent, water, acetone, and then isopropyl alcohol (IPA); and then dried in an oven at 80° C. for about 30 min under an ambient environment. Substrates were then baked at about 200° C. for about 1 hour in an ambient environment, then under UV-ozone treatment for about 30 minutes. PEDOT:PSS (hole-injection material) was then spin-coated on the annealed substrate at about 4000 rpm for about 30 sec. The coated layer was then baked at about 100° C. for 30 min in an ambient environment, followed by baking at 200° C. for 30 min inside a glove box ($N_2$ environment). The substrate was then transferred into a vacuum chamber, where 4,4'-bis[N-(naphthalenyl)-N-phenyl-amino]biphenyl (NPB) was vacuum deposited at a rate of about 0.1 nm/s rate under a base pressure of about $2\times10^{-7}$ torr. Bis(1-phenylisoquinoline)(acetylacetonate)iridium(III) ("Ir(piq)$_2$acac") (6 wt %) was co-deposited as an light-emitting layer with Host-1 host material at about 0.01 nm/s and about 0.10 nm/s, respectively, to make the appropriate thickness ratio.

1,3,5-Tris(1-phenyl-1H-benzimidazol-)-2-yl)benzene (TPBI) was then deposited at about 0.1 nm/s rate on the light-emitting layer. A layer of lithium fluoride (LiF) (electron injection material) was deposited at about 0.005 nm/s rate followed by deposition of the cathode as Aluminium (Al) at about 0.3 nm/s rate. The representative device structure was: ITO (about 150 nm thick)/PEDOT:PSS (about 30 nm thick)/NPB (about 40 nm thick)/Host-1: Ir(piq)$_2$acac (about 30 nm thick)/TPBI (about 30 nm thick)/LiF(about 0.5 nm thick)/Al (about 120 nm thick). The device was then encapsulated with a getter attached glass cap to cover the light-emitting area of the OLED device in order to protect from moisture, oxidation or mechanical damage.

Each individual device had an area of about 13.2 mm$^2$.

Example 3

Device Performance

Example 3.1

Figure 2:
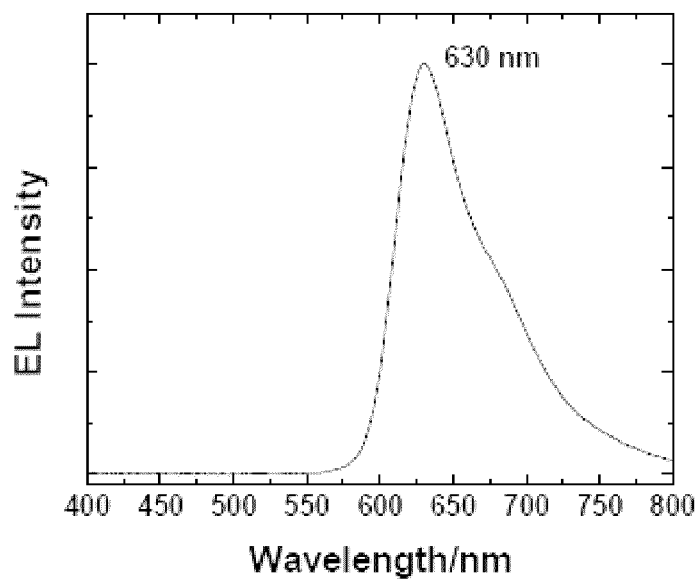
FIG. 2 is an electroluminescent spectrum of a device comprising a compound disclosed herein.
Figure 3:
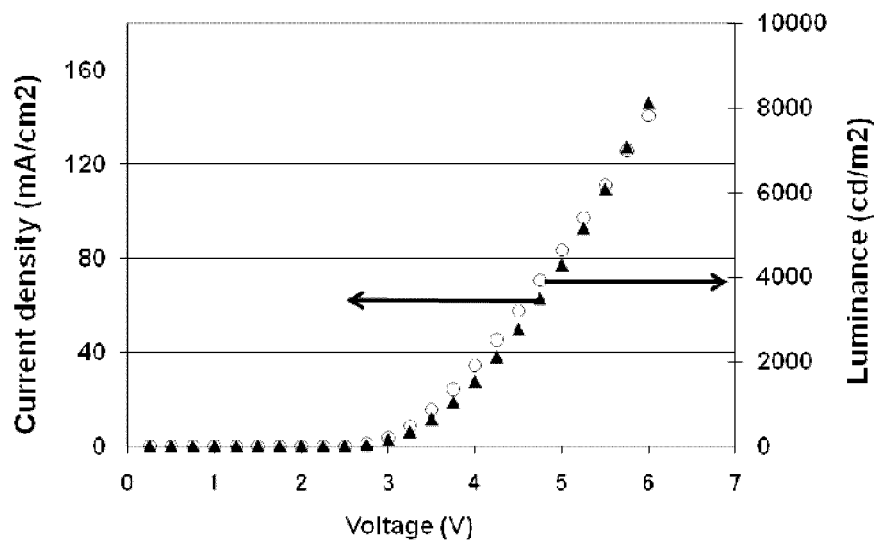
FIG. 3 is a plot of current density and luminance as a function of driving voltage for an embodiment of an OLED comprising a compound disclosed herein.
Figure 4:
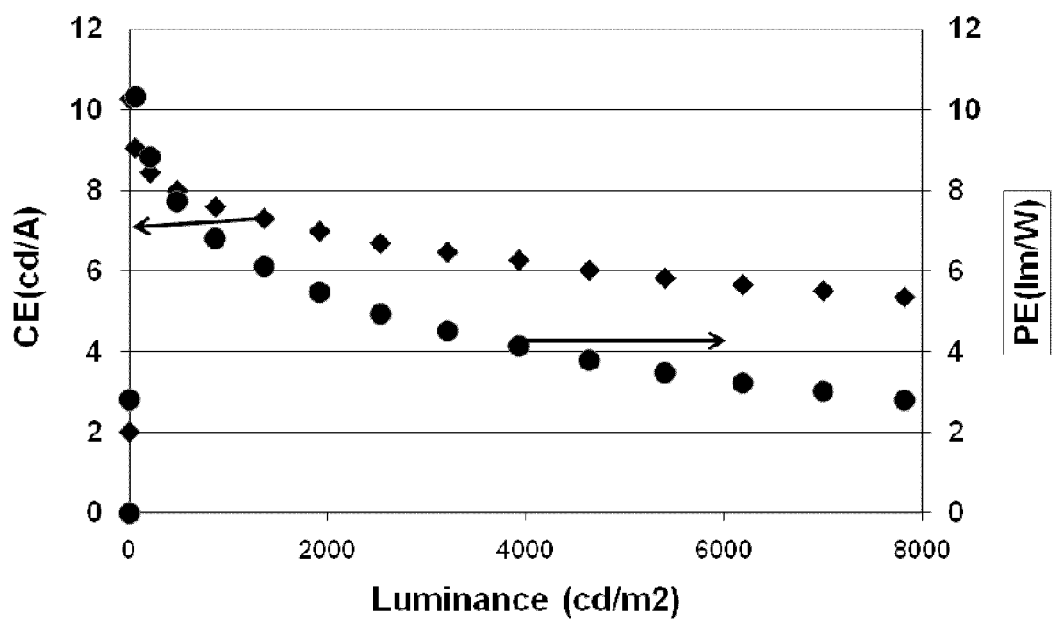
FIG. 4 is a plot of current efficiency and power efficiency as a function of luminance for an embodiment of an OLED comprising a compound disclosed herein.

All spectra were measured with a PR670 spectroradiometer (Photo Research, Inc., Chatsworth, Calif., USA), and I-V-L characteristics were taken with a Keithley 2612 SourceMeter (Keithley Instruments, Inc., Cleveland, Ohio, USA). All device operation was performed inside a nitrogen-filled glove-box. Device A, a red light emitting device, comprising Host-1: Ir(piq)$_2$acac and fabricated in accordance with Example 2.1, was tested to determine the emissive qualities of the device by examining the current density and luminance as a function of the driving voltage, as shown in FIG. 2. The turn-on voltage for the device was about 2.5 volts and the luminance was about 8,000 cd/m$^2$ with 13.2 mm$^2$ area device at about 6V.

TABLE 1

| Device | PE (Lm/w) | LE (cd/A) |
|---|---|---|
| Device A | 9.8 | 10.4 |

Thus Compound Host-1 has demonstrated its effectiveness as a host material in organic light emitting devices.

Example 3.2

Device A, a light emitting device comprising Host-1: Ir(piq)$_2$acac, and fabricated in accordance with Example 2.1, was tested to determine the lifetime of the devices (T$_{50}$(h) at 10,000 nit). Other devices (Comparative Device X [Bebq2], and Comparative Device Y [CBP]) were constructed in accordance to Example 2.1, except that, for the respective

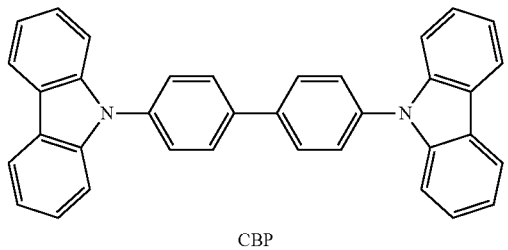

CBP

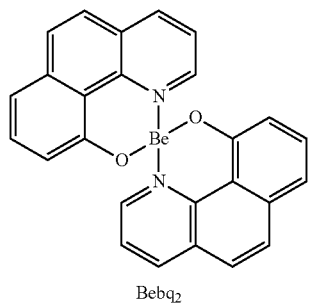

Bebq$_2$ devices, Comparative Compound X, Bis(10-hydroxybenzo[h]quinolinato)beryllium (Bebq$_2$ (94%), and Bis(1-phenylisoquinoline)(acetylacetonate)iridium(III) ("Ir(piq)$_2$acac") (6%), and Comparative Compound Y, 4,4'-bis(carbazol-9-yl)biphenylCBP (94%), and Bis(1-phenylisoquinoline)(acetylacetonate)iridium(III) ("Ir(piq)$_2$acac") (6%) were co-deposited on top of NPB, respectively, to form a 30 nm thick light-emitting layer 20.

All spectra were measured with an PR670 spectroradiometer (Photo Research, Inc., Chatsworth, Calif., USA) (and I-V-L characteristics were taken with a Keithley 2612 SourceMeter (Keithley Instruments, Inc., Cleveland, Ohio, USA). All device operation was performed inside a nitrogen-filled glove-box without encapsulation.

Table 2 shows the device lifetime of devices fabricated in accordance to Examples 2.2 and 2.3.

| Device | T50(h) @ 10000 nit |
|---|---|
| Device A | 200 |
| Comparative Device X | 100 |
| Comparative Device Y | 6 |

Thus at least Host-1 has demonstrated its effectiveness as a long lasting compound in light emitting organic light emitting devices.

Although the claims have been described in the context of certain preferred embodiments and examples, it will be understood by those skilled in the art that the scope of the claims extend beyond the specifically disclosed embodiments to other alternative embodiments and/or uses and obvious modifications and equivalents thereof.

What is claimed is:
1. A compound represented by a formula:
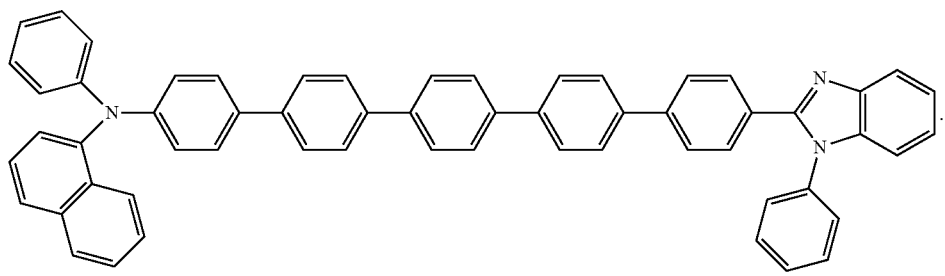 [SMILES: c1ccc(N(c2ccc(-c3ccc(-c4ccc(-c5ccc(-c6ccc(-c7nc8ccccc8n7-c7ccccc7)cc6)cc5)cc4)cc3)cc2)c2cccc3ccccc23)cc1]
2. A light-emitting device comprising a compound of claim 1.
3. The light-emitting device of claim 2, wherein the compound is in a light-emitting layer.
* * * * *